United States Patent [19]
Esteves et al.

[11] Patent Number: 5,873,212
[45] Date of Patent: Feb. 23, 1999

[54] STAND ALONE SWAGE DIAL DRIVE ASSEMBLY

[75] Inventors: Anthony Esteves, Somerville; David D. Demarest, Parsippany, both of N.J.

[73] Assignee: Ethicon, Inc., Somerville, N.J.

[21] Appl. No.: 847,154

[22] Filed: Apr. 30, 1997

[51] Int. Cl.$^6$ ................................................ B65B 63/04
[52] U.S. Cl. ........................... 53/118; 53/116; 53/113; 53/147; 53/249
[58] Field of Search .................... 53/113, 116, 118, 53/249, 430, 147, 238; 206/63.3

[56] References Cited

U.S. PATENT DOCUMENTS

| | | | |
|---|---|---|---|
| 5,473,810 | 12/1995 | Demarest et al. | 53/118 |
| 5,473,854 | 12/1995 | Demarest et al. | 53/116 |
| 5,477,609 | 12/1995 | Demarest et al. | 53/118 |
| 5,487,212 | 1/1996 | Demarest et al. | 53/118 |
| 5,661,954 | 9/1997 | Ivanov et al. | 53/118 |
| 5,664,404 | 9/1997 | Ivanov et al. | 53/118 |

*Primary Examiner*—James F. Coan
*Assistant Examiner*—Gene L. Kim

[57] ABSTRACT

A semi-automated machine for singulating individual surgical needles from an bulk supply and attaching a suture to the surgical needle is described. The machine includes a needle singulation station, a precise positioning station, a suture feeding station, a swage station, a pull-test station and an off-load station. A universal gripper mounted on a rotary indexing device automatically receives each individual needle in a predetermined orientation and conveys the needle for sequential processing from station to station to form the needle-suture assembly. The rotary indexing device is driven by a single shaft drive assembly which provides a compact annular drive from two intermittent indexing drives to two coaxial cam dials that provide rotation and reciprocation of the universal gripper. A swage station is provided for swaging the needle to close the suture receiving opening about the suture to secure said suture thereto and form therefrom a needle and suture assembly. A final off-load station provides an apparatus for assembling a predetermined number of need-suture assemblies in a bundle for subsequent packaging.

25 Claims, 19 Drawing Sheets

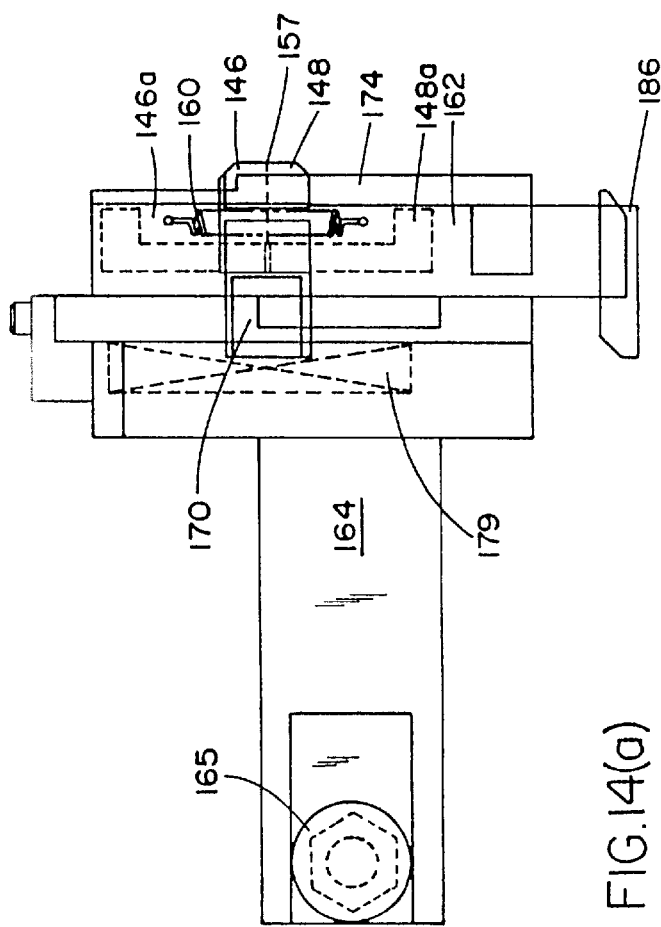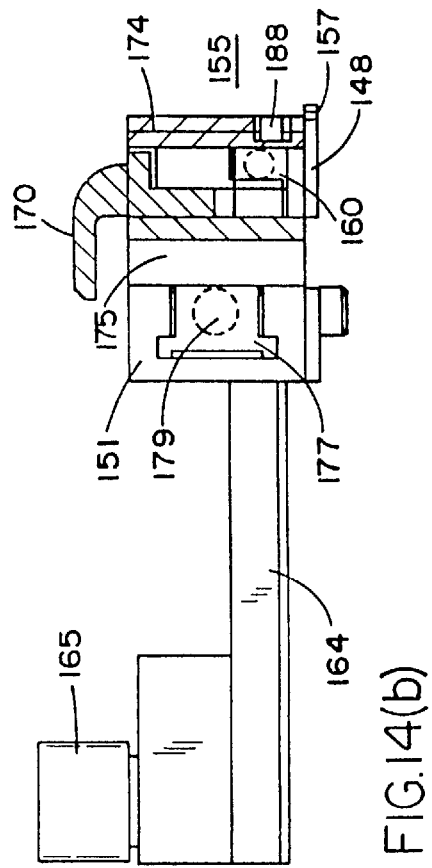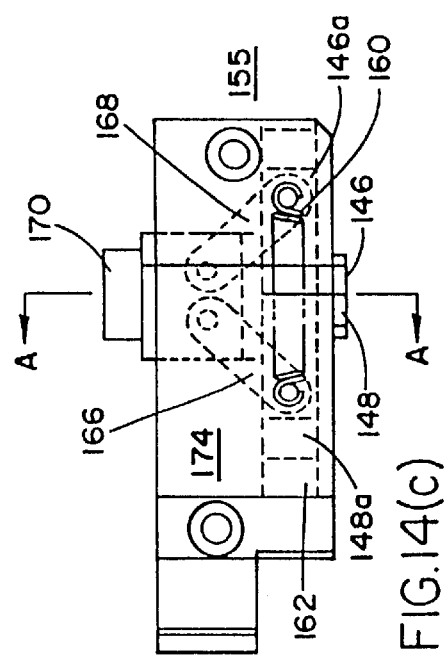

STAND ALONE SWAGE DIAL DRIVE ASSEMBLY

FIELD OF THE INVENTION

The present invention relates generally to machines for automatically swaging needles, such as surgical needles to a suture, and more specifically, to an apparatus that automatically swages, tests, and creates bundles of armed sutures, i.e., needles having a suture strand of predetermined length attached at one end thereof, for subsequent packaging.

DESCRIPTION OF THE PRIOR ART

This application describes in detail an improvement of a portion of the apparatus disclosed in a series of U.S. Patents, of which U.S. Pat. No. 5,473,810 entitled "Needle-Suture Assembly and Packaging System" and U.S. Pat. No. 5,473,854 entitled "Machine for the Automated Packaging of Needles and Attached Sutures and Method of Utilizing the Packaging Machine," are typical. All of these patents are assigned to the assignee of the present invention.

The present application claims improvements in the drive train for the swage dial and improvements in the operation of the swage dial, which functions in a manner similar to the swage dial used in the machine described in the aforesaid patents.

The automatic needle and suture threading machine described in U.S. Pat. Nos. 5,473,810 and 5,473,854 is a highly automated machine intended for high volume production and packaging of needles and sutures wherein 20,000 to 40,000 needles and sutures are to be produced in a single run.

SUMMARY OF THE INVENTION

The present invention is directed to a standalone swage machine that is particularly adapted to assist in the semiautomated singulation of surgical needles to enable subsequent automated handling of the needle, automatic swaging, automatic pull testing of the combined needle and suture, and bundling for future packaging.

It is an object of the present invention to provide a machine which will efficiently handle small batches or production runs on needles and to efficiently handle premium needles and super sharp cutting edge needles in an efficient manner without blunting the cutting edge of the needle.

It is another object of the present invention to provide a machine which is flexible in operation and enables quick changeovers between production lots and which minimizes the number of change parts required to migrate from one size needle or suture to another.

It is another object of the present invention to provide a machine which will handle odd runs or "doctors' specials" as they are referred to in the trade, where a particular surgeon expresses a preference for an unusual combination of needle type or size and suture material.

It is an objection of the present invention to provide a needle threading and swaging apparatus for attaching a suture to a surgical needle having a suture receiving opening formed therein, wherein the apparatus includes a frame which supports a drive means for a swage dial. The drive means includes a first and a second intermittent drive, each of which intermittent drives have a drive period and a dwell period to provide intermittent advancement of the swage dial. The machine includes a swage dial and a cam dial mounted for rotation about a common first axis of rotation, with the swage dial supported by and mounted for rotation on a first drive shaft which rotates about this single first axis of rotation. This first drive shaft is driven by said first intermittent drive to provide intermittent advancement of the swage dial.

It is another object of the present invention to provide a plurality of universal gripper mounted on said swage dial for successively receiving an individual one of a plurality of precisely positioned needles at a first predetermined location and indexing each of said individual successive needles in a predetermined orientation from said first predetermined location through successive locations for sequential processing at subsequent predetermined locations, each of said universal grippers having a cam follower which cooperates with said cam dial to provide radial reciprocation of said universal grippers with respect to said swage dial in response to rotation of said cam dial.

It is another object of the present invention to provide an annular drive shaft which is co-axially mounted on said first drive shaft, with the annular drive shaft supporting and coupling the second intermittent drive and said cam dial for rotation about said first axis.

It is another object of the present invention to provide universal grippers are rotated by said swage dial to each of said predetermined locations and reciprocated in and out of an operative position by said cam dial at each of said plurality of predetermined locations.

Finally, it is an object of this invention to provide needle and suture assemblies (armed sutures) that are bundled by the present machine for subsequent packaging in machines such as that typified by U.S. Pat. No. 5,487,212 or the machine described in U.S. Ser. No. 521,831, entitled "Single Suture Automated Packaging Machine", both of which are assigned to the assignee of the present invention.

BRIEF DESCRIPTION OF THE DRAWINGS

FIG. 11(a) is detailed top view of the cam dial assembly 120 having cam dial plate 125 with cam follower 165a in a retracted position within cam track 160a.

FIG. 11(b) is cut away top view of the cam dial plate 125 showing cam follower 165a in an extended position within cam track 160a.

FIG. 14(a) is top plan view of the universal gripper and slide assembly used in the present invention, illustrating in dotted lines the various operating components thereof.

FIG. 14(b) is partially cross-sectioned side view of the universal gripper and slide assembly illustrated in FIG. 14(a).

FIG. 14(c) is a partially hidden front view of the universal gripper illustrated in FIG. 14(a) illustrating in dotted lines the actuating mechanism used to open the jaws of the universal gripper.

DETAILED DESCRIPTION OF THE PREFERRED EMBODIMENT

The present invention is directed to a standalone swage machine that is particularly adapted to assist in the semiautomated singulation of surgical needles to enable subsequent automated handling of the needle, automatic swaging, automatic pull testing of the combined needle and suture, and bundling for future packaging.

This application describes in detail an improvement of a portion of the apparatus disclosed in U.S. Pat. No. 5,473,810 entitled "Needle-Suture Assembly and Packaging System" and U.S. Pat. No. 5,473,854 entitled "Machine for the Automated Packaging of Needles and Attached Sutures and Method of Utilizing the Packaging Machine," both assigned to the assignee of the present invention. The present invention includes an improved drive train for the swage dial which is similar to the swage dial used in the machine described in the aforesaid patents.

The automatic needle and suture threading machine described in U.S. Pat. No. 5,473,810 is a highly automated machine intended for high volume production and packaging of needles and sutures wherein 20,000 to 40,000 needles and sutures are to be produced in a single run.

The machine described in this application is designed to efficiently handle small batches or production runs on needles and to efficiently handle premium needles and super sharp cutting edge needles in an efficient manner. It is intended to provide flexibility in operation and a quick changeover between production lots and to minimize the number of change parts required to migrate from one size needle or suture to another.

The present invention is also intended to handle odd runs or "doctors' specials" as referred to in the trade, where a particular surgeon expresses a preference for an unusual combination of needle type or size and suture material.

Needle and suture assemblies (armed sutures) are bundled by the present machine for subsequent packaging in machines such as that typified by U.S. Pat. No. 5,487,212 or the machine described in U.S. Ser. No. 521,831, entitled Single Suture Automated Packaging Machine, both of which are assigned to the assignee of the present invention.

Figure 2:
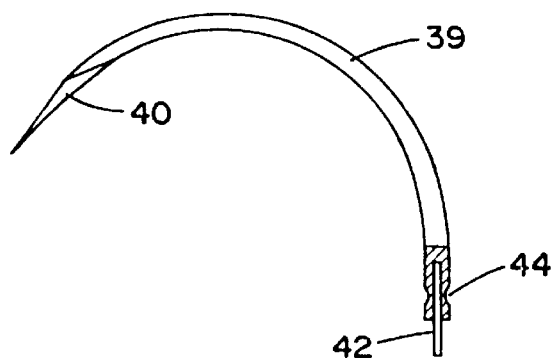
FIG. 2 is a diagrammatic view of an edged needle that is typical of the needles to be singulated and swaged according to the present invention.

The present invention minimizes the handling of the needle and is therefore particularly adapted for the automated handling of premium needles and cutting edge needles such as the needle illustrated in FIG. 2.

As illustrated in FIG. 2, the needle 39 includes a ground or cutting edge portion 40 and is illustrated with an attached suture 42 which has been attached by swaging as indicated at 44. The suture 42 may be of any predefined length, but is commonly provided in lengths that are multiples of nine inches (18, 27 and 36 inch suture sizes are particularly common).

Figure 1:
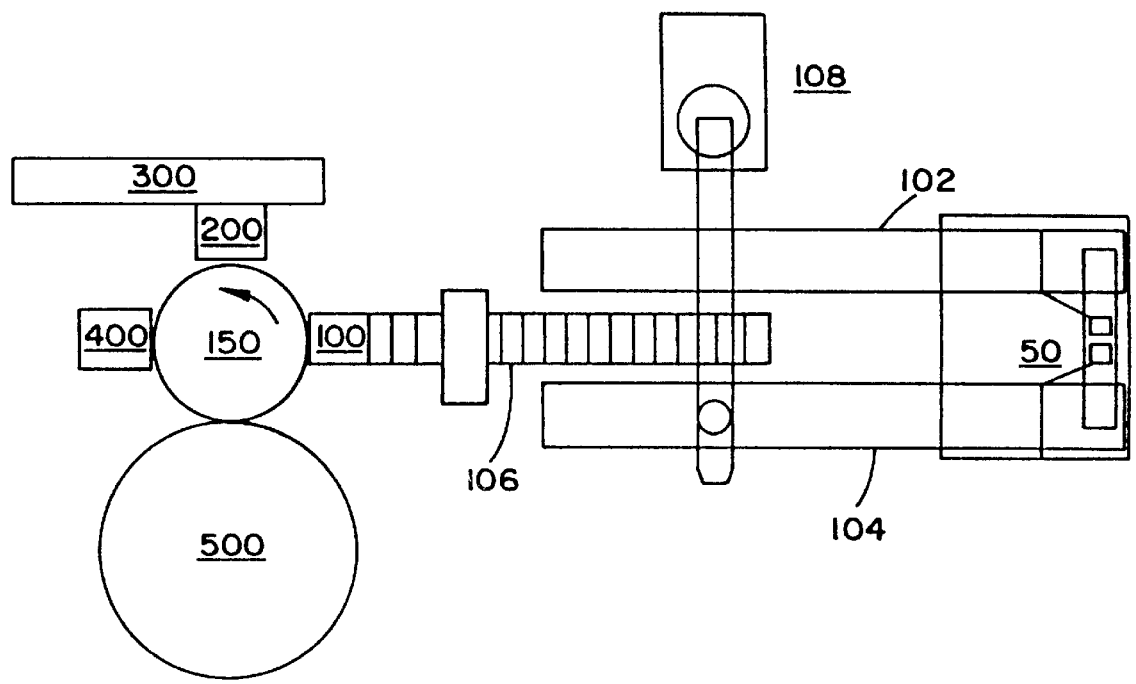
FIG. 1 is a diagrammatic top view of the needle threading and swaging system incorporating a semi-automatic needle sorting and singulating table for feeding individual needles to a universal gripper mounted on a rotary swage dial, an automatic swaging station, an automatic pull-test station, and an armed suture off-load and bundling station.

Generally, in the needle threading and swaging system of the present invention, parallel operations take place simultaneously at a plurality of different stations to ensure that approximately forty to sixty (40–60) armed surgical needles are assembled and discharged per minute. For instance, as shown in FIG. 1, a semi-automatic needle sorting and singulating station 50 assists an operator in sorting and singulating individual needles to a pair of translucent indexing conveyors 102,104 where the singulated needles are imaged by a vision system, selected by a computer, and transferred from the translucent indexing conveyors 102,104 to a precision indexing conveyor 106 by a robotic gripper 108. The precision indexing conveyor conveys precisely oriented surgical needles to a precise positioning station 100 to be sequentially received by a plurality of grippers mounted on the rotary swage dial 150. The rotary swage dial then rotates counter-clockwise as shown by the arrow in FIG. 1, to index each needle to the automatic swaging station 200 where the suture material is cut, inserted into the needle, and automatically swaged thereto. A suture drawing and cutting station 300 pulls, tips, cuts and inserts the suture into the needle to be swaged. The needle is swaged and then, the rotary swage dial 150 rotates to index the armed suture to the automatic pull-test station 400 where each armed needle is pull-tested to ensure that the minimum and/or destructive pull-test requirements of the medical profession, are met. Finally, the rotary swage dial indexes the pull-tested armed needle to the off-load station 500 where the surgical needle and suture assemblies are handed off for suture bundling for subsequent packaging at another location.

Figure 3A:
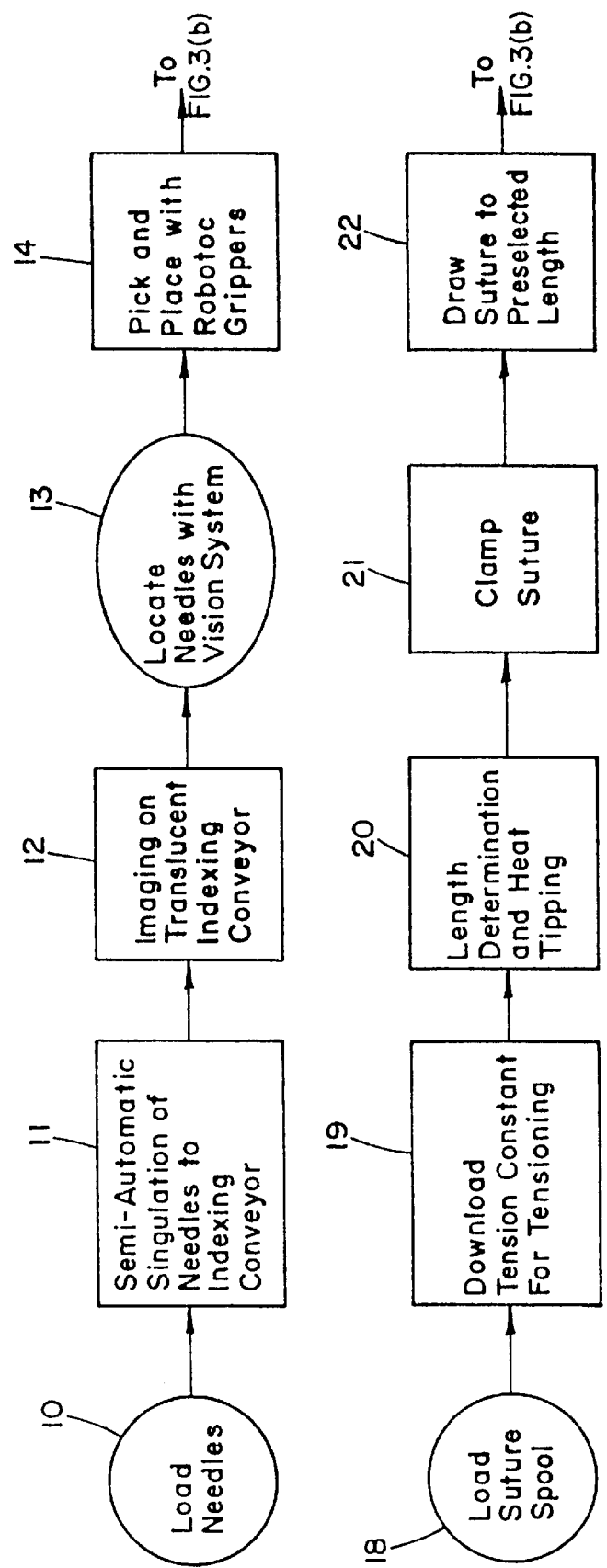
FIGS. 3(a), 3(b) and 3(c) together form a flow diagram illustrating the process for the needle threading and swaging system of the present invention.
Figure 3B:
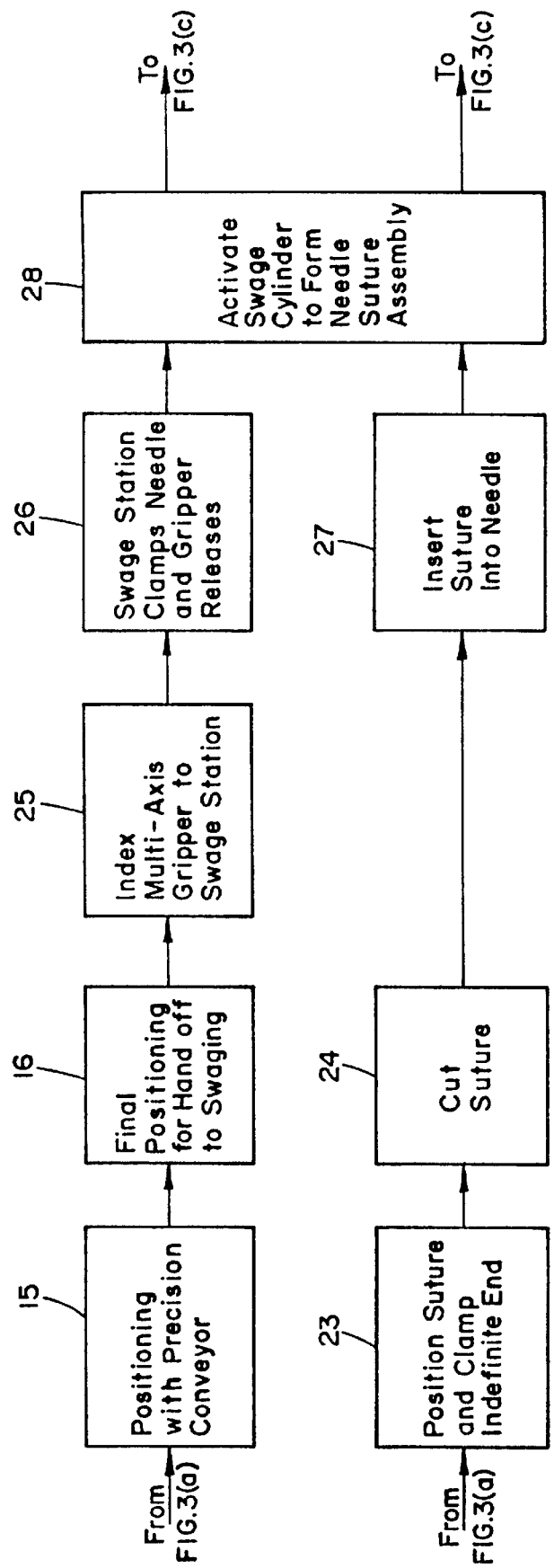
Figure 3C:
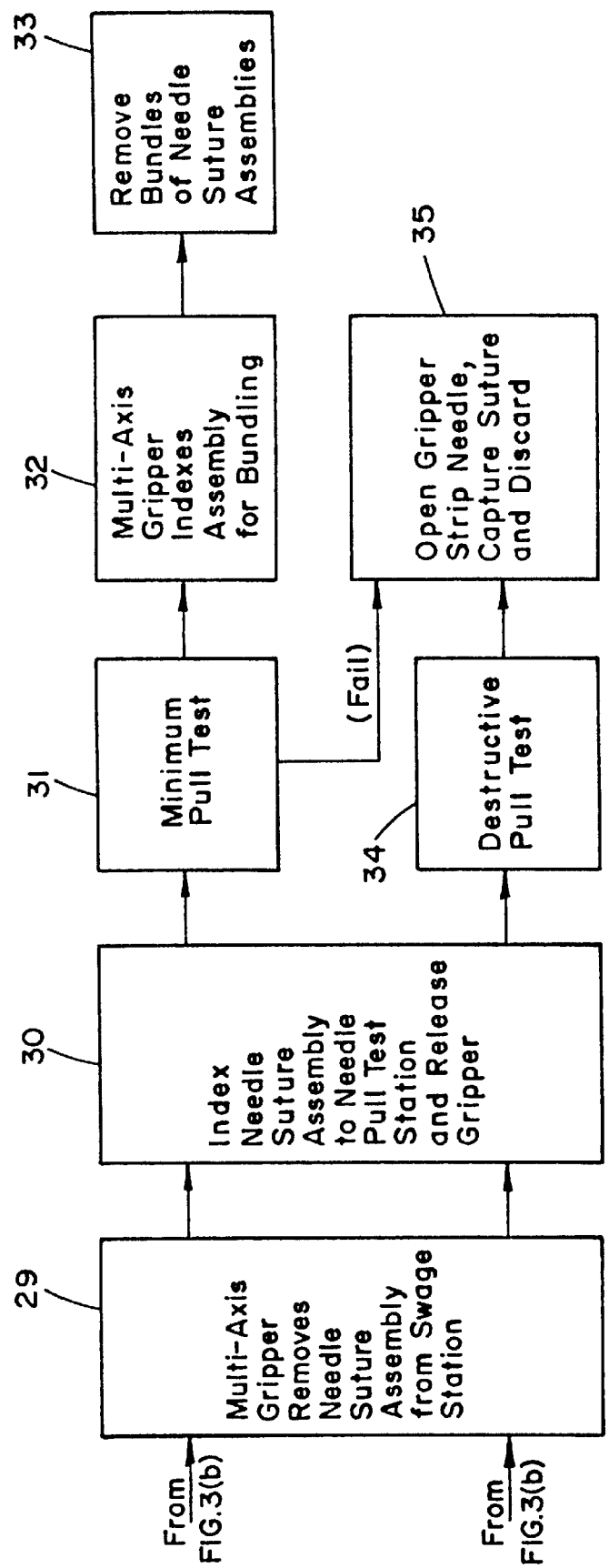

FIGS. 3(a) through 3(c) are block diagrams which illustrate the automatic needle threading and swaging process of the instant invention. For instance, at the needle singulating station 50, needles are first loaded onto a flat operator work surface at 10, singulated by the operator, and then automatically and individually fed at step 11 to one of the translucent indexing conveyors 102,104. The needles are imaged at step 12 and then evaluated with respect to orientation and position by a vision tracking system at step 13, picked up by a robot apparatus at step 14, transferred to a precision conveyor 106 for positioning by the robot apparatus 108 at step 15, and finally conveyed to a load station 100 where the needles are precisely positioned at step 16 and transferred to a universal gripper located on a rotary swage dial 150 for subsequent transfer to the swaging station 200 indicated at step 25. A detailed explanation of the apparatus used to carry out each step will be explained in further detail hereinbelow.

Simultaneous with the needle sorting process described above with respect to steps 10 through 25, an automatic suture cutting process takes place at the suture station 300 as shown in FIGS. 3(a) and 3(b) with respect to steps 18 through 28. Indefinite length suture material is supplied in various spools and configurations that may carry up to 5000 yards of material. This is indicated at step 18 in FIG. 3(a), where the suture material is loaded into a payoff assembly. A tension constant for the suture to be drawn is downloaded as indicated at step 19. A drawing tower apparatus includes grippers that alternately draw lengths of the suture material from the spool to enable cutting thereof which lengths are predetermined at step 20.

While the material is being drawn, it may require extra treatment or processing. For instance, as described in detail below, it may be desirable to heat the suture material under tension at the area which will become the suture tip in order to stiffen the material to facilitate the positioning thereof within the suture receiving opening of a surgical needle. Thus, at step 20, heat may be applied to a portion of suture material. In the preferred embodiment of the invention the heating step is performed upstream of the drawing and cutting apparatus to enable the suture to partially cool and harden before cutting. At step 21 of the block diagram of FIG. 3(a), the suture material is clamped and gripped by the servo grippers, and at step 22, the suture strand is drawn to a predetermined length and positioned for insertion within the suture receiving opening of the needle for swaging. As the suture is positioned for insertion, a second suture clamps the suture at a position which will hold the indefinite length end at step 23, and the suture is cut at step 24 to separate the suture of predetermined length from the indefinite length suture.

After a surgical needle is indexed to the swaging station 200 as described above, the universal gripper positions the needle in a precisely oriented position at the swage die opening formed at the ends of two swaging dies of a swage assembly as indicated as step 26 in FIG. 3(b). Simultaneously, the suture strand is drawn along a suture axis to register a tip thereof for insertion within the suture receiving end of the needle. Next, at step 27, the gripper assembly at the drawing tower inserts the tip of the suture strand within a lower funnel guide for accurate positioning within the suture receiving opening of the needle that is aligned with the suture drawing axis. At step 28, the swage cylinder is activated to automatically swage the suture to the needle. The universal gripper is actuated to grip the needle, and then retracted on the rotary swage dial as shown as step 29 and indexed to a pull-test station 400 at step 30 so that minimum pull-testing at step 32 or destructive pull-testing at step 34 may be performed.

Depending upon the results of the minimum pull-test, the needle and suture assembly will either be indexed by the rotary swage dial to the off-load station 500 where the armed needle will be bundled if the pull-test requirements are met (as shown as step 32 in FIG. 3(c)), or, will be discharged at the pull-test station if the needle fails the minimum pull-test (as shown as step 35 in FIG. 3(c)). The destructive pull-test always renders the needle incapable of further processing so the needle is automatically discharged at the pull-test station 400 as indicated at step 35 in FIG. 3(c). Finally, as shown as step 33 in FIG. 3(c), needle and suture assemblies passing the minimum pull test are conveyed to an off-load station 500 where the individual armed sutures are bundled for subsequent packaging and sterilization.

A detailed explanation of the apparatus used to carry out each step in the suture cutting process will be explained in further detail hereinbelow.

Overview of the Apparatus

Figure 4:
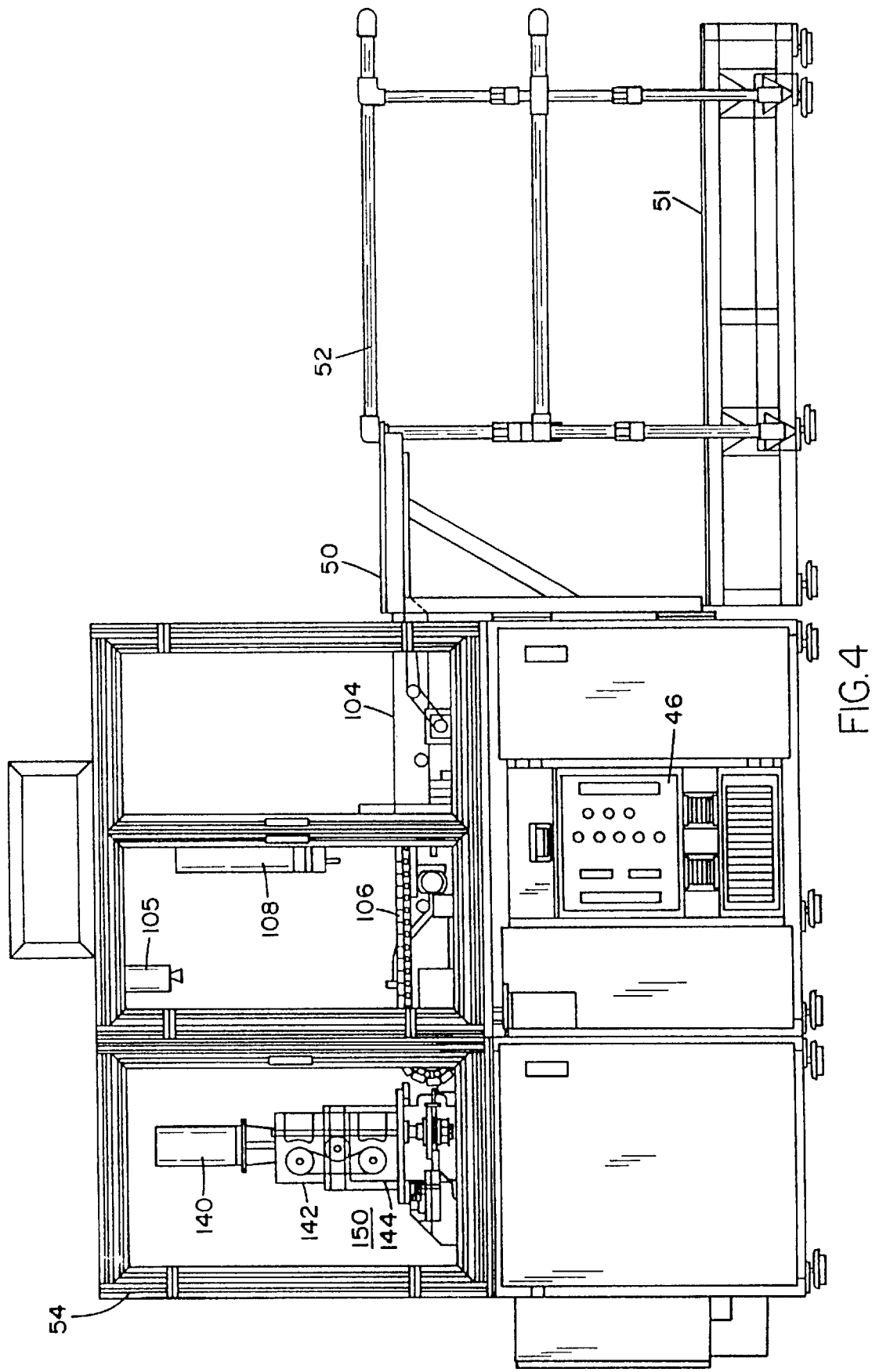
FIG. 4 is an elevation side view of the present invention illustrating an operator station, a control computer, portions of the robotic handling device, and the swage drive of the present invention.
Figure 5:
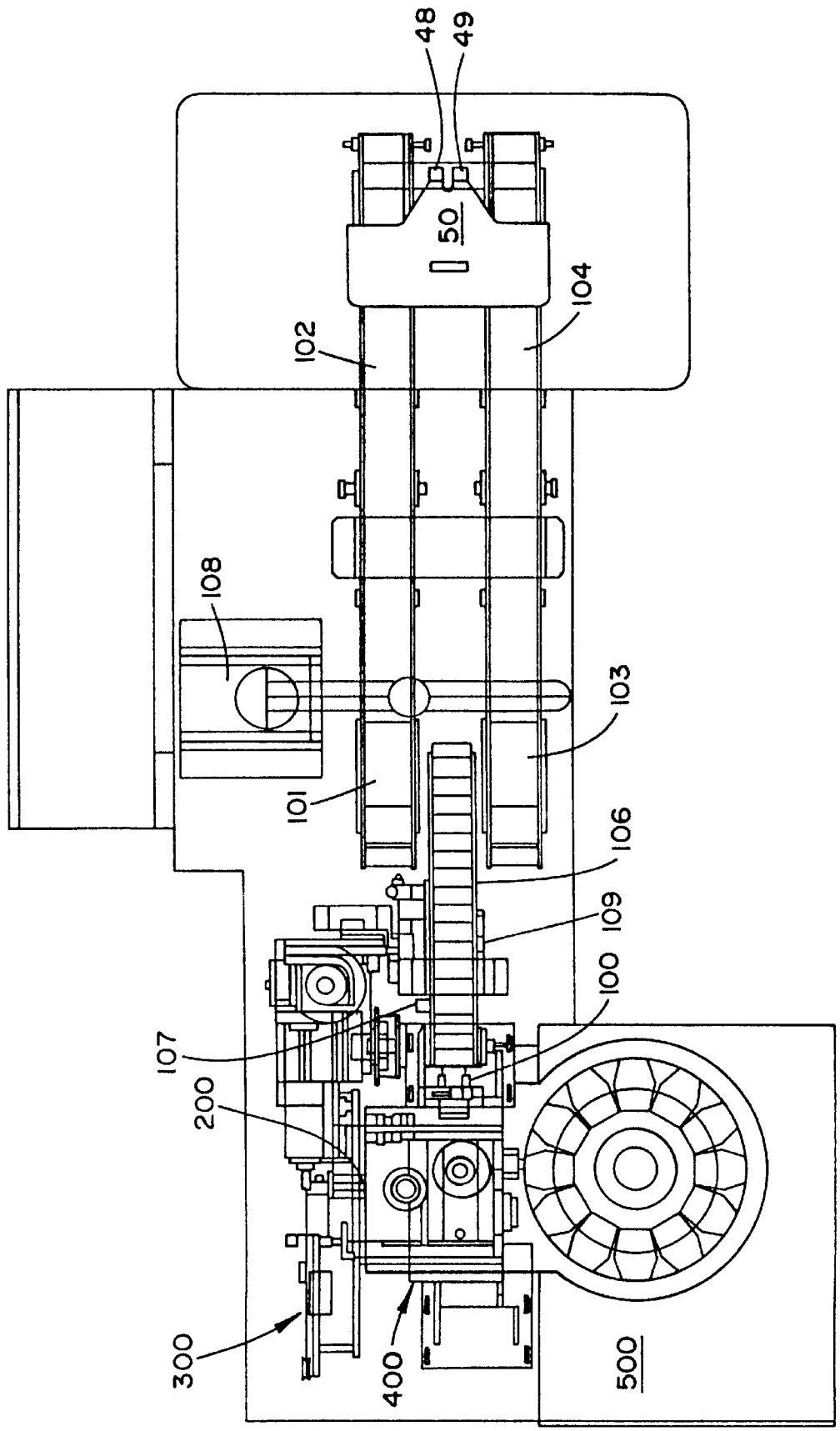
FIG. 5 is a top plan view of the present invention with the operator safety guards illustrated in FIG. 4 removed.
Figure 6:
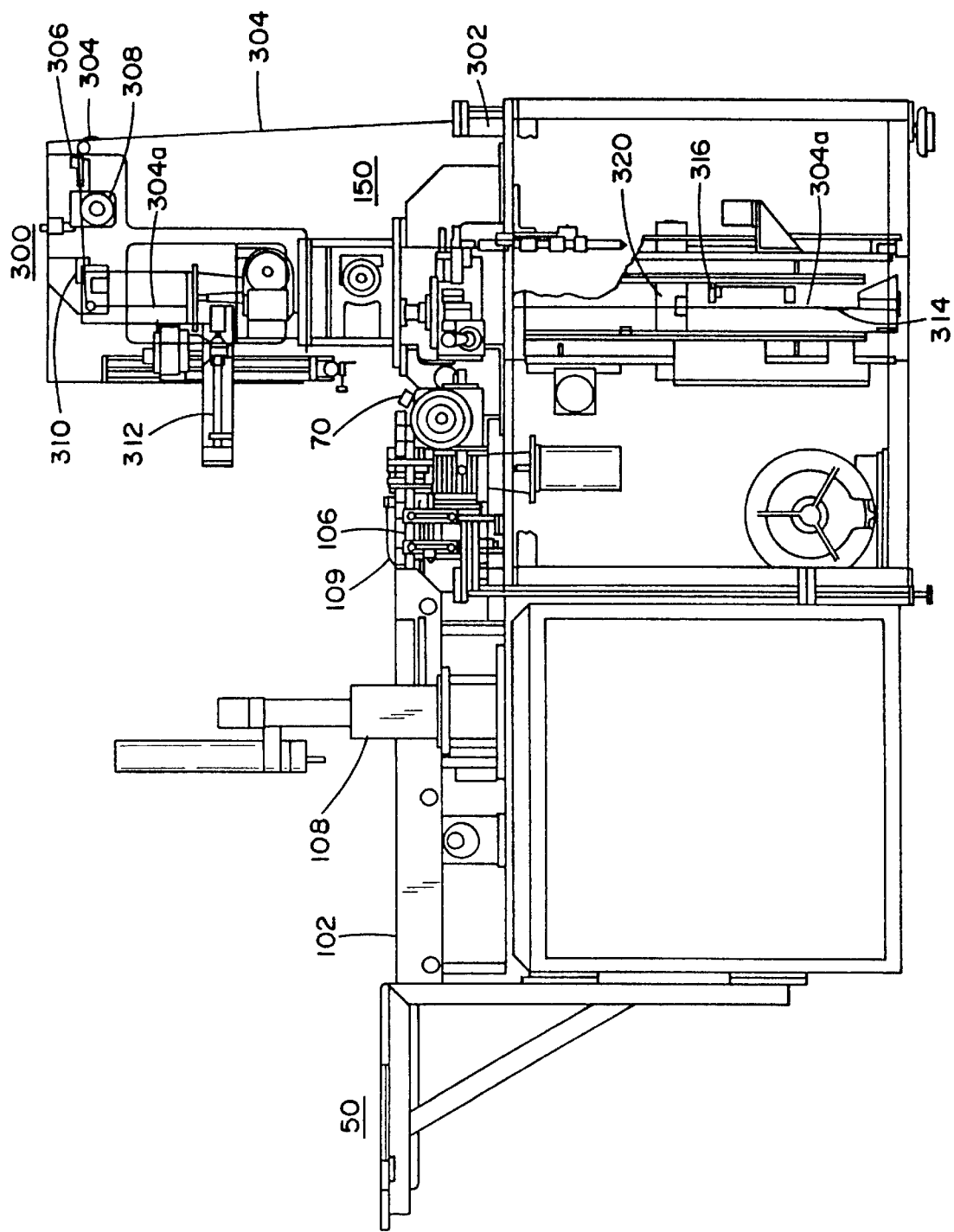
FIG. 6 is a detailed elevation side view of the present invention from the opposite side as illustrated in FIG. 4, with the operator safety guards removed.

FIG. 4 is an elevation view of one side of an apparatus constructed according to the teachings of the present invention, and FIG. 5 is a top plan view of the apparatus with the safety guards removed. FIG. 6 illustrates the apparatus from the opposite side as FIG. 4. FIGS. 4–6 are used in the following descriptive overview of the apparatus. This apparatus includes a singulation area or table 50 to assist an operator in singulating needles that are deposited to the translucent conveyors 102,104, one of the conveyors 104, being depicted in FIG. 4. The operator work station includes a platform 51 for operator seating and guard rails 52 for operator safety. Safety guards 54 are also provided around the machine for safety purposes.

Each of the needles singulated by the operator are dropped through openings 48,49 by sliding the needle along the table surface 50. This step avoids the needle to needle contact inherent in the vibratory feed bowls illustrated in U.S. Pat. No. 5,473,810 and thus substantially reduces the risk that premium needles or cutting edge needles will be blunted by needle contact. As each needle is dropped, the drop is sensed by a sensor, and at an appropriate interval, the needles is blown by a puff of air to the translucent indexing conveyor, with needles dropped through opening 48 being transferred to translucent indexing conveyor 102 and needles being dropped through opening 49 being transferred to translucent indexing conveyor 104.

The needles thus transferred are indexed forward to imaging stations 101,103 wherein a back light provides a high contrast image of the needle against a white background for imaging purposes. The indexing conveyors 102, 104 are indexed approximately 2 inches at each index, and more precisely approximately 3 times the cord length of the needle. By limiting the incremental advancement the image processing is step is enhanced, and problems associated with inertial loads on the needles on conveyors 102,104 are minimized. If the indexing conveyors 102,104 are accelerated too quickly, the needle will remain in its drop position and not be advanced forward, and conversely, if the needle is moving on the conveyor, and the conveyor is stopped too quickly, the needle will continue to travel after the conveyor is stopped. The present apparatus seeks to avoid either of these situations by minimizing the amount of index at each incremental step while still providing enough movement to provide an adequate supply of needles to the apparatus.

The needle singulating apparatus illustrated provides a single needle at each drop point which substantially enhances the accuracy of the vision system and minimizes needle returns that might otherwise be necessary for overlapping or nested needles that were either not imaged, or selected by the computer control means 39 for transfer by the robotic apparatus 108.

The needles deposited on the translucent indexing conveyor 104 are imaged by a vision system 105 and these images are processed by a computer control means 46 to identify the orientation and X,Y coordinate location of the needles. Determining the X,Y coordinates alone is not enough in the needle swaging environment inasmuch as the robotic apparatus needs to determine, in the case of a symmetrically formed curved needle, which end is the barrel end and which end is the cutting end in order to properly place the needle for subsequent automated handling. After both the orientation and location have been determined, a robotic apparatus 108 picks the needles from the translucent conveyors 102,104 and places them on a precision indexing conveyor 106. The precision conveyor 106 includes a plurality of "boats" 70 which are particularly adapted to provide precision positioning of the needle. The rotary swage dial 150 includes a drive motor 140 and first and second indexing transmissions 142,144 which are used to drive the swage dial in a manner as will be hereinafter explained in detail.

The needles transferred by the robotic apparatus 108 are transferred so that the butt end of the needle 44 is engaged by gripping jaws on the conveyor boats 70 of the precision conveyor 106. While the butt end is located and gripped by the robotic apparatus 108, at the point of pickup it may be oriented in either direction of curvature. For particularly small needles a fixed post may be provided for the robotic apparatus to use in correcting the orientation of curvature. For larger needles, a needle plow 109 is used so that the direction of curvature for each of the needles is uniform. As illustrated in FIG. 5, the apparatus also includes a prepositioner 107 which is adapted to approximately locate the butt end of the needle and an adjustable hard stop assembly at station 100 that precisely registers the butt end of the needle to an accuracy of 0.001 inches.

The needle singulation apparatus, and the operation of the indexing conveyors 102,104, the robotic apparatus 108 and the precision conveyor 106 is more fully described and claimed in U.S. Ser. No. 08/847,133, entitled "Semi-Automated Needle Feed Method and Apparatus," the disclosure of which is incorporated herein by reference thereto.

After the needle has been received at the precise positioning station 100, it is gripped by one of the universal grippers located on the swage dial mechanism 150 to be indexed through a plurality of stations including a swage station 200 wherein a suture of definite length is cut from a suture spool of indefinite length at station 300 and inserted into the needle at swage station 200 for permanent assembly thereto. After swaging, the needle is advanced to the pull-test station 400 for testing of the needle suture bond, and then indexed to a bundling station 500 wherein a plurality of buckets are circumferentially arranged on a rotating turntable to receive a predefined number of needles and sutures in each bundle.

Figure 13:
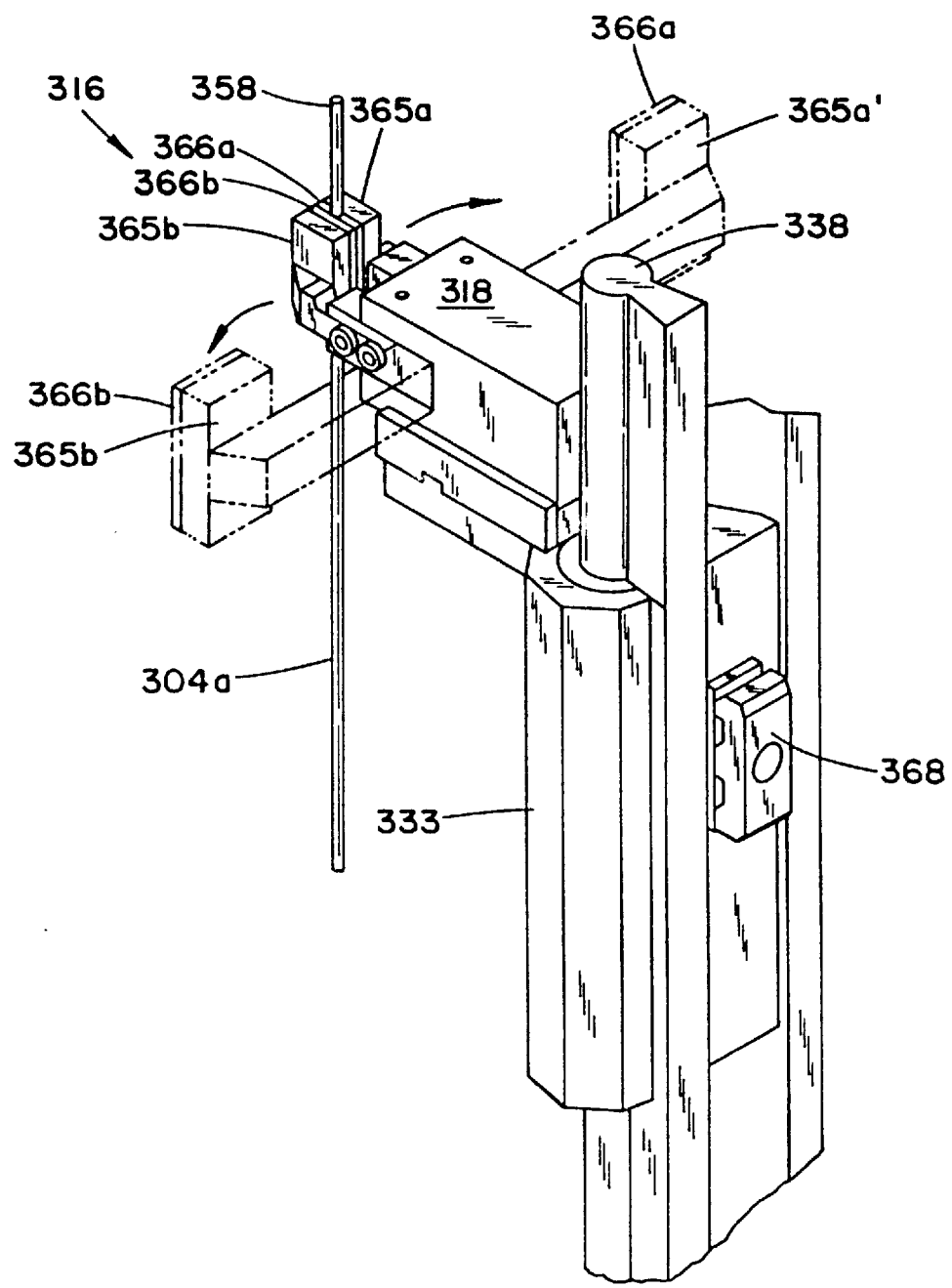
FIG. 13 is an enlarged isometric view of a suture gripper assembly having gripper arms shown in their open (dotted lines) and closed (suture gripping) positions.

FIG. 6 illustrates the apparatus of the present invention from the opposite side of the machine illustrated in FIG. 4 and includes breakaway portions to more particularly illustrate portions of the precision conveyor apparatus and the suture drawing and cutting station 30C. As illustrated in FIG. 6, a spool of suture material 302 is mounted on a convenient location and the indefinite length suture material 304 is fed to the suture drawing station through a pretensioning apparatus 306, a tensioning roller 308 having a computer controlled tension constant which may be selectively downloaded from the computer control means 46 to match the suture material 304 being handled, and a knot detector 310 which may be used to shut down the machine in the event the suture material becomes tangled. From the knot detector 310 the suture strand 304a is fed through a tipping station 312 which heats the suture strand to a predetermined temperature to assist in tipping and cutting the suture for insertion into the surgical needle. From the heating and tipping station 312, the suture material is passed to the bottom of the machine to a turnaround roller 314 where it is grasped by first and second suture clamps which advance the suture material 304a in a hand over hand manner. As illustrated in FIG. 13, clamp 316 includes a traveling carriage 333 which reciprocates up and down frame member 338 by means of a timing belt which is secured to the carriage at 368. A pneumatic actuator 318 includes first and second clamps 365a,365b and first and second gripping surfaces 366a,366b which clamp the suture material therebetween.

Figure 15:
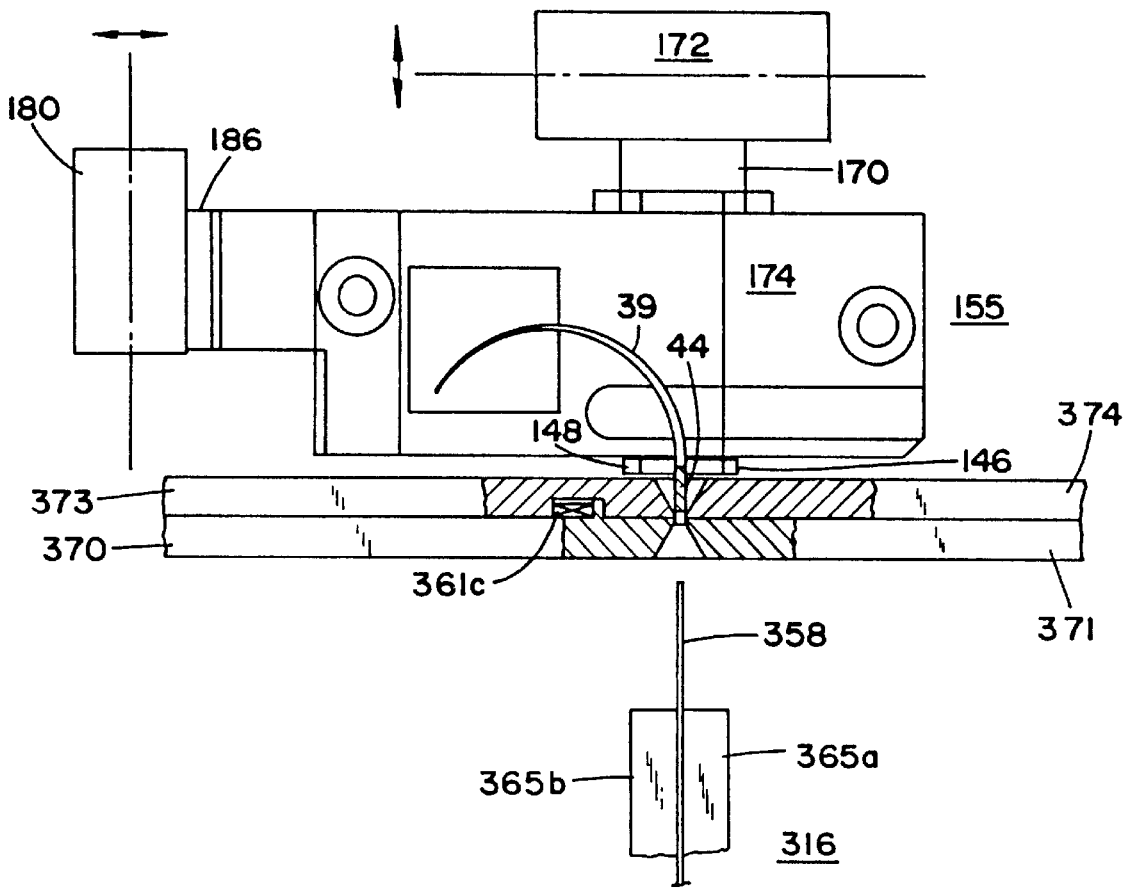
FIG. 15 is front face view of the universal gripper showing a surgical needle in a relaxed engagement, with the needle gripped by the swage dies of the present invention.

In a first cycle of operation, clamp 316 draws the suture of indefinite length to a suture insertion point immediately adjacent the swage plates of the swaging station and then dwells while a second suture clamp clamps the indefinite suture length below the suture cutter 320 illustrated in FIG. 6. After the second suture clamp has engaged the suture, the cutter 320 is actuated to cut the suture and the tip end of the suture 358, illustrated in FIG. 13 is inserted into the needle as illustrated in FIG. 15. The tip end of the suture 358 is positioned below a funnel dye formed in suture alignment plates 370,371 which reciprocate immediately below swage plates 373,374. After the suture tip end 358 has been inserted into the barrel end 44 of needle 39, the swage station is actuated driving the swage plate 374 against swage plate 373 to swage the suture tip 358 to the surgical needle 39. The suture drawing, tipping and cutting is more completely described in U.S. Ser. No. 08/804,478, U.S. Ser. No. 08/803,573, and U.S. Ser. No. 08/804,477, all of which are entitled "Suture Cutting System," the disclosures of which are incorporated herein by reference thereto.

The Swage Dial Drive Assembly

Figure 7A:
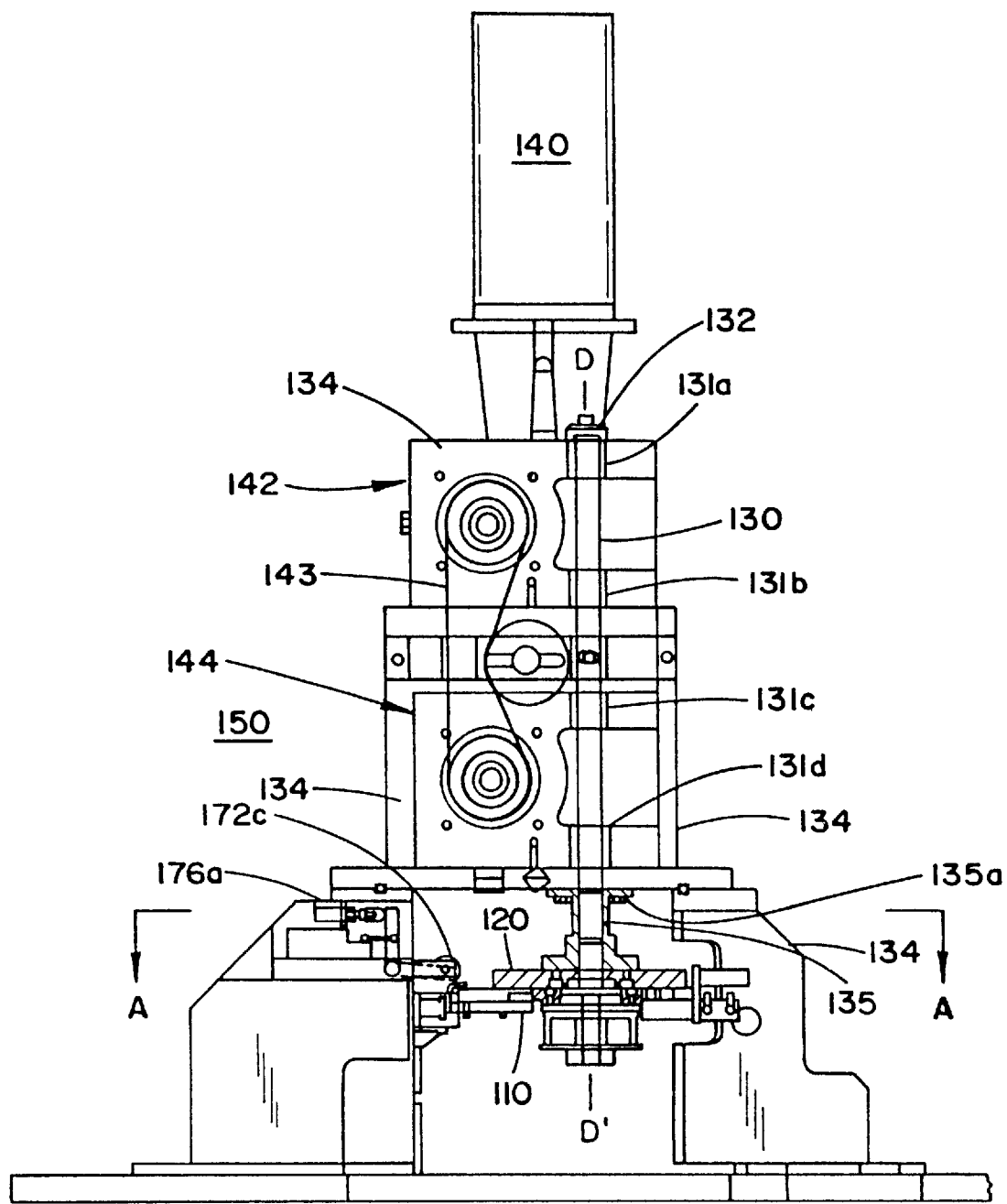
FIG. 7(a) is an elevation view of a portion the apparatus illustrating the inventive drive for the cam dial and swage dial of the present invention.
Figure 7B:
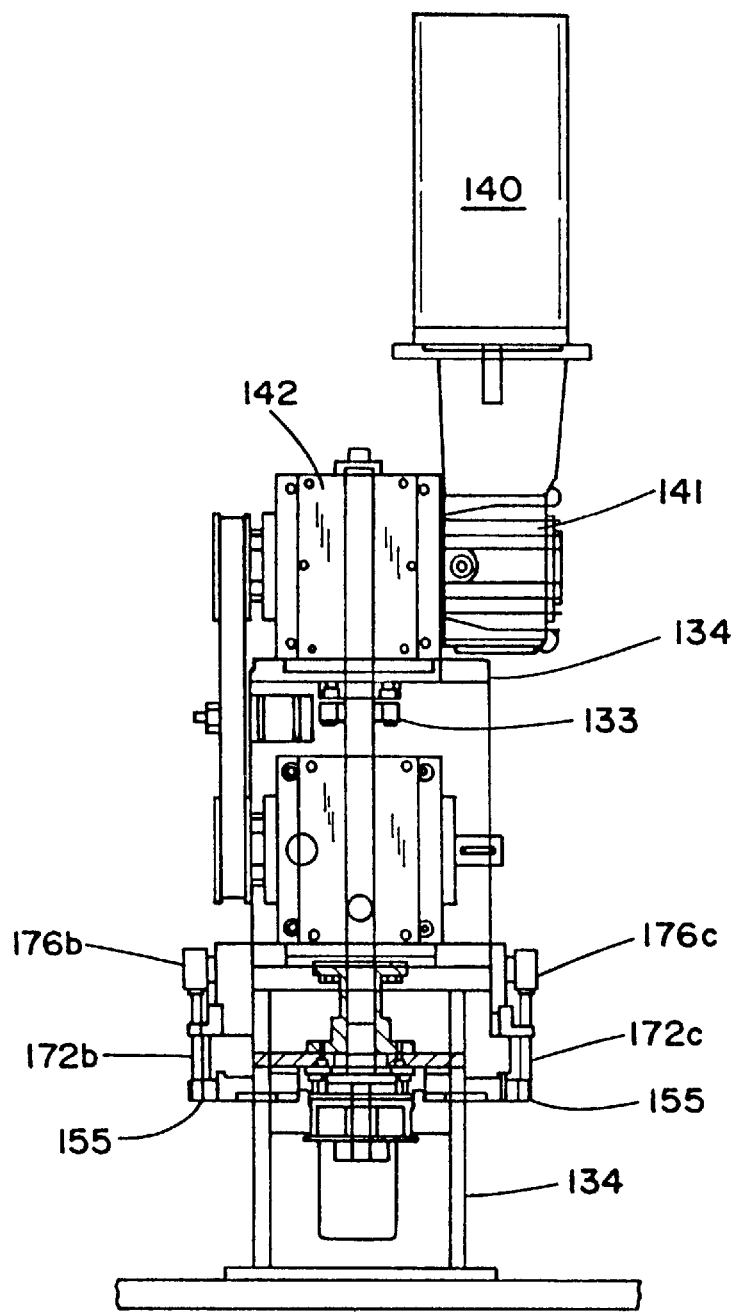
FIG. 7(b) is a side view of the drive for the swage dial illustrated in the elevation view of FIG. 7(a).
Figure 8:
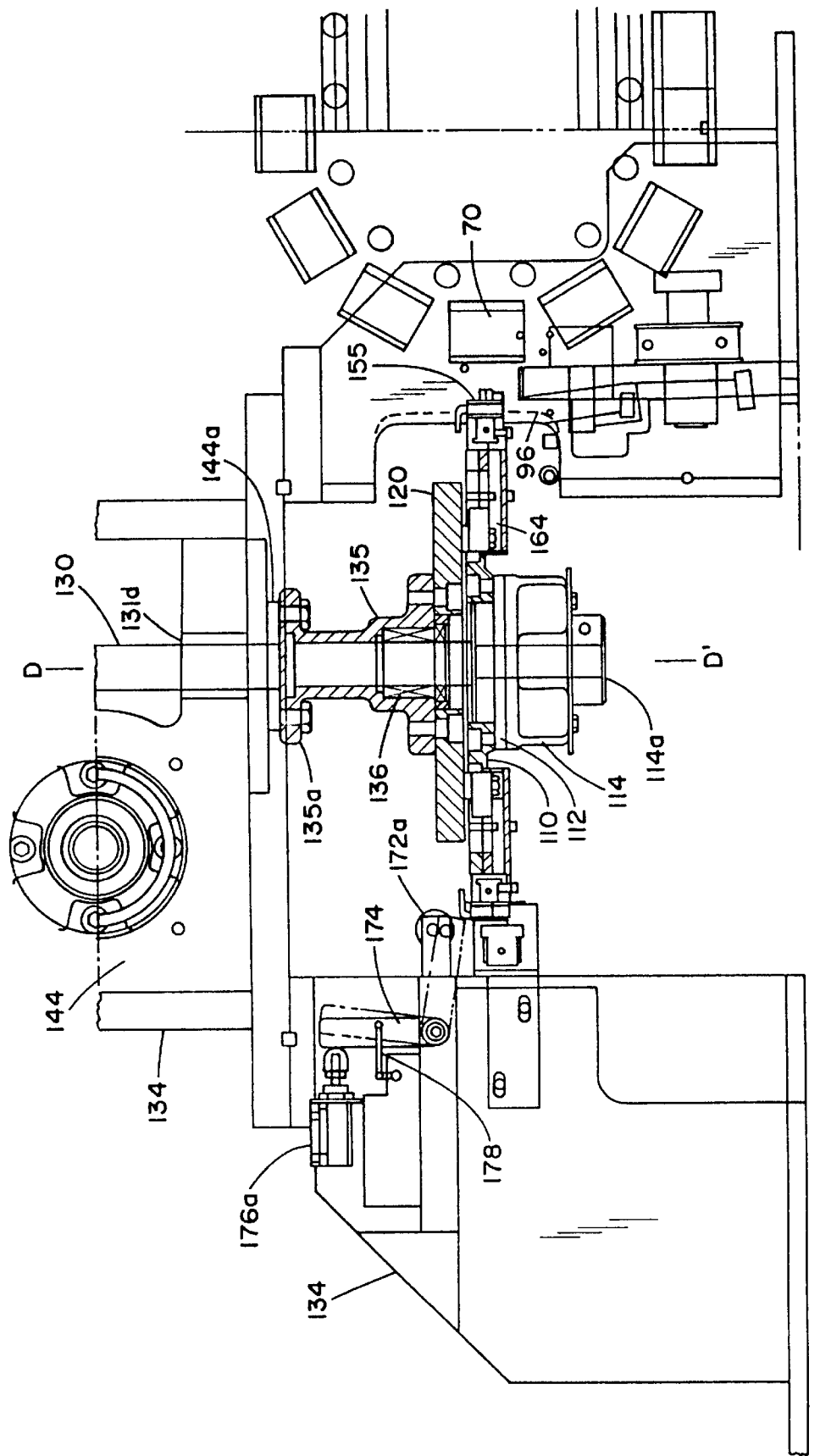
FIG. 8 is a detailed and partially cross section view of the drive for the swage dial taken along section lines "A"—"A" in FIG. 7(a) which illustrates a universal gripper ready to reciprocate outwardly to receive an oriented surgical needle from a precision conveyor.
Figure 9:
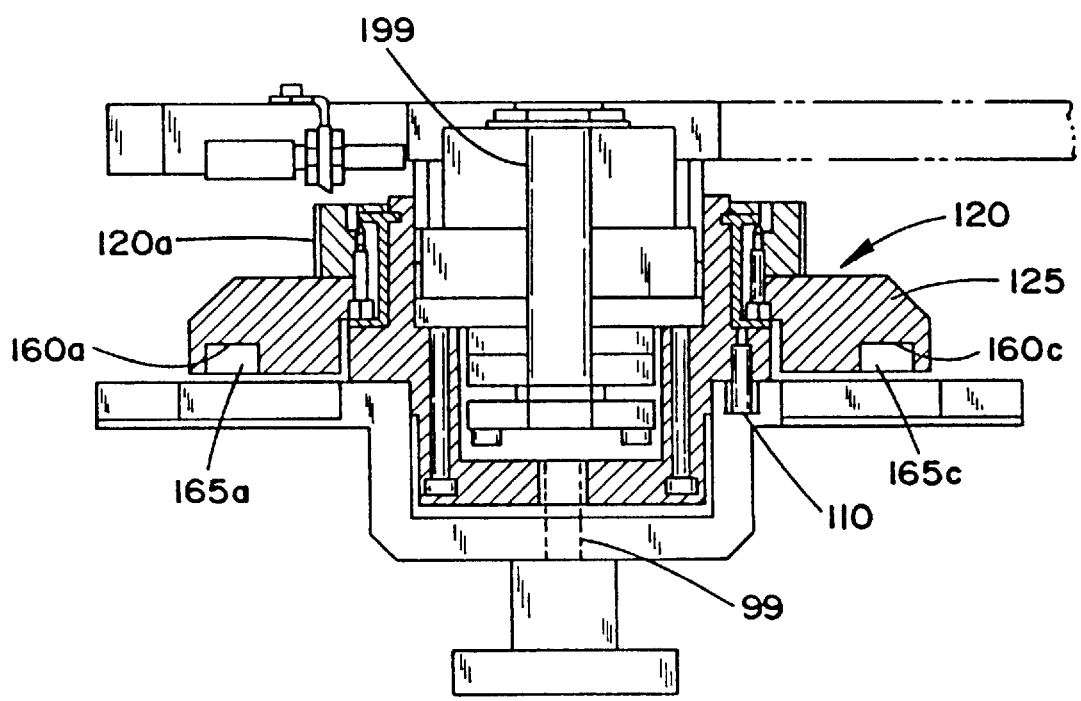
FIG. 9 is a side view of a prior art drive for a swage dial as illustrated in U.S. Pat. No. 5,473,810.

The drive assembly for the swage dial 150 is illustrated in FIGS. 7a, 7b and 8, and the differences between the drive for the swage dial assembly and the drive of the prior art may be seen by comparing FIG. 8 with FIG. 9.

As illustrated in FIG. 7a, the swage dial assembly 150 includes a swage dial 110 and a cam dial assembly 120 both of which are independently driven by the drive means of the present invention. A drive motor 140 drives both of these dials through a first indexing drive transmission 142 and a second indexing drive transmission 144 through a 90° reduction transmission 141 (illustrated in 7b) and are coupled together with a timing belt 143. The indexing drive assemblies 142,144 are "CAMCO" Indexer Drivers Model 350RGD 4H24-360 with a 10 to 1 reduction in transmission 141 and an oscillation motion for the cam dial assembly 120. As will be hereinafter explained with respect to FIGS. 10–11, the first indexing CAMCO drive includes 180° of drive and 180° of dwell for every revolution of the transmission drive 141 which results in a 90° drive dwell cycle for the first indexing drive 142. The first indexing drive 142 drives shaft 130 about a single drive axis D–D' illustrated in FIGS. 7–8. It is journalled for rotation in bearings 131a,b,c, and d and is secured in place by drive cap 132 and a compression drive collar 133 which is connected to the output of the first indexing drive 142. A modular frame assembly 134 supports each of the drive elements about the central drive axis D–D'.

The second indexing drive 144 also includes 180° of drive, then 60° of drive, 30° of dwell, a second 60° of drive and a 30° dwell for each revolution of the input drive from belt means 143, and the indexing drive 144 is phased with the drive and dwell cycles of the first drive 142. As will be hereinafter described with respect to FIGS. 10 and 11, during each dwell period of the swage dial 110, the cam dial assembly 120 is held in a dwell position and then rotated to enable radial reciprocation of the universal grippers with respect to the swage dial 110.

The cam dial assembly 120 is mounted on an annular drive collar 135 which connects the output of the second indexing drive 144 to the cam dial plate 120 as more fully illustrated in FIG. 8. The annular drive 135 is journalled for rotation on drive shaft 130 by means of needle bearings 136 to provide a single drive access D–D' for rotation of the swage dial assembly 110,120. The annular drive collar provides suspension support and rotational drive for the cam dial assembly 120. The use of this annular collar also separates the cam dial and swage dial from the drive apparatus and enables operator workspace for alignment of the apparatus and for part changes when necessary. The annular drive collar 135 is bolted to the output drive flange of the indexing drive 144 as shown at 135(a).

The swage dial 110 is mounted for rotation on a ball detent clutch 114 which is fixably attached to shaft 130 and enables breakaway rotation between clutch drive plates 112 and 114 in the event of a catastrophic jam. The clutch 114 and shaft 130 also provide suspension support and rotational drive for the swage dial 110.

The annular cam drive 135 is bolted to the output of the second indexing drive 144 as illustrated at 135a and thus provides for both suspension support and rotation of the cam dial assembly 120. Likewise, the breakaway clutch 114 provides physical support and rotational drive for the swage dial 110 by virtue of its fixed mounting on shaft 130 at 114a.

The prior art drive assembly illustrated in FIG. 9 involved a pair of nested coaxial drives which was substantially more complex than the drive of the present invention. In the embodiment illustrated in FIG. 9, a servo motor was used to drive the cam dial assembly 120 through timing belt pulley 120(a). The swage dial was driven from shaft 199 which was an integral part of the indexing drive. In a subsequent improvement to the apparatus of FIG. 9, a second indexing drive was added for the cam dial assembly (not shown), but the cam dial was bolted directly to the output of the second index drive, and did not afford any operator workspace which made it very difficult to service and align the dials, or to change parts.

The physical dimensions of the drive of the present invention have also been substantially reduced to enable work space around the swage dial for alignment and change parts operations when necessary.

The Swage Dial

Figure 10A:
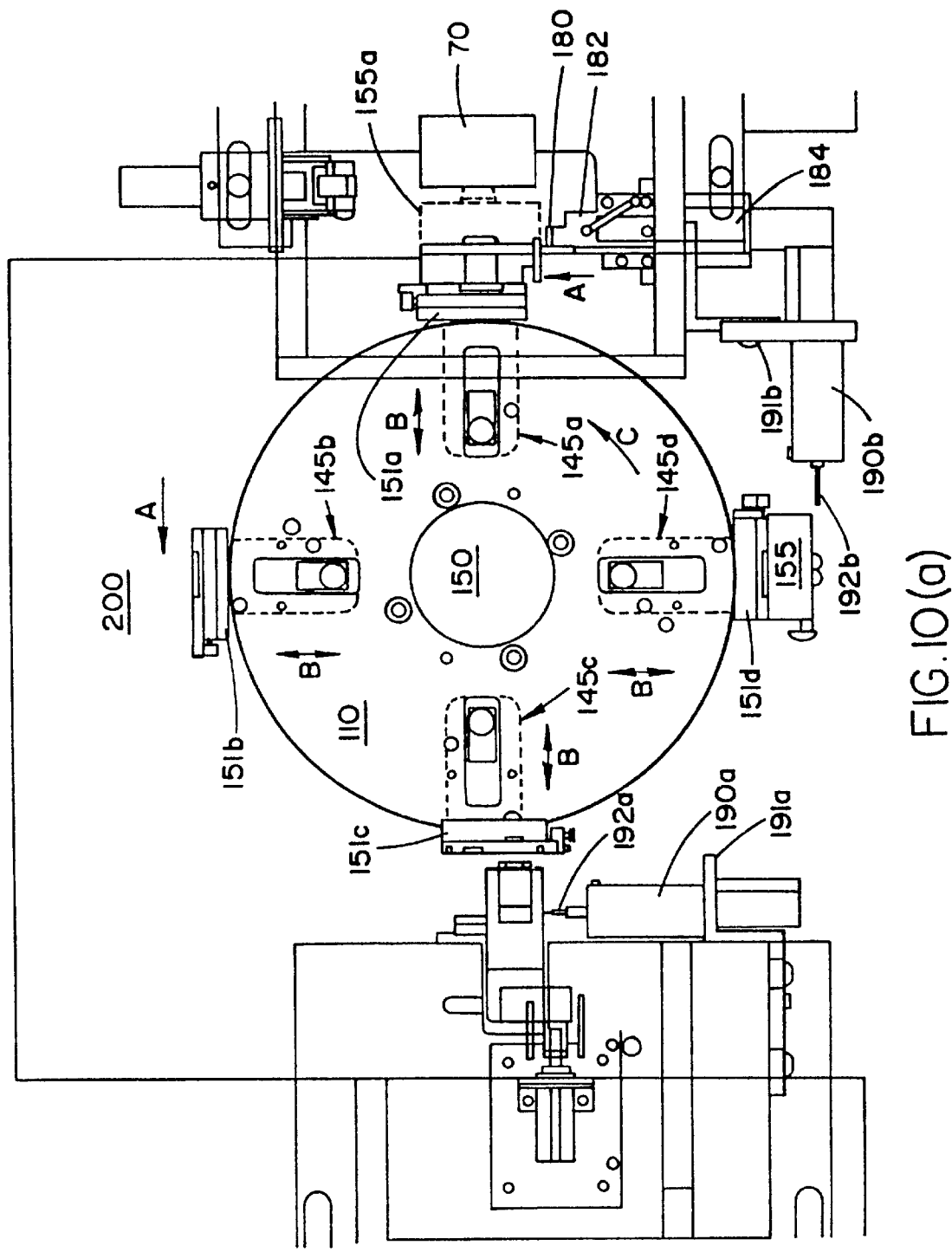
FIG. 10(a) is a top view of the swage dial assembly 150 comprising a swage dial plate 110 having four universal gripper stations 145a, b, c, d mounted thereon.
Figure 10B:
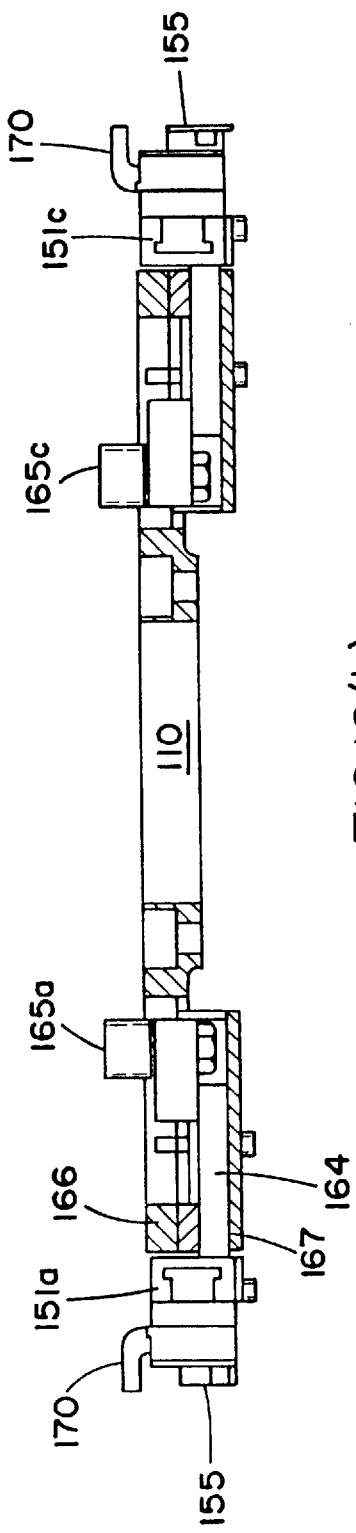
FIG. 10(b) is cross-sectional view of the four station swage dial assembly 150 showing universal gripper 155 in a retracted position.
Figure 10C:
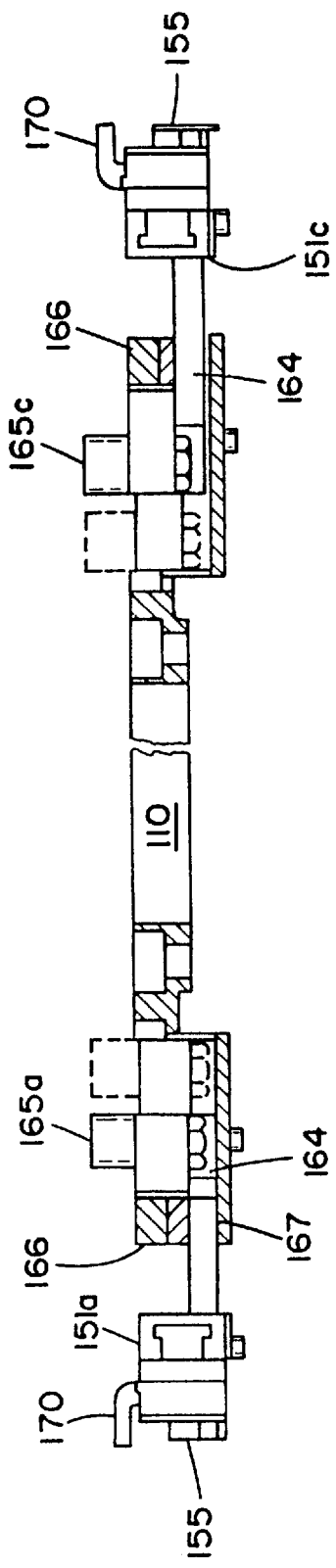
FIG. 10(c) is cross-sectional view of the four station swage dial assembly 150 showing universal gripper 155 in an extended position.
Figure 11A:
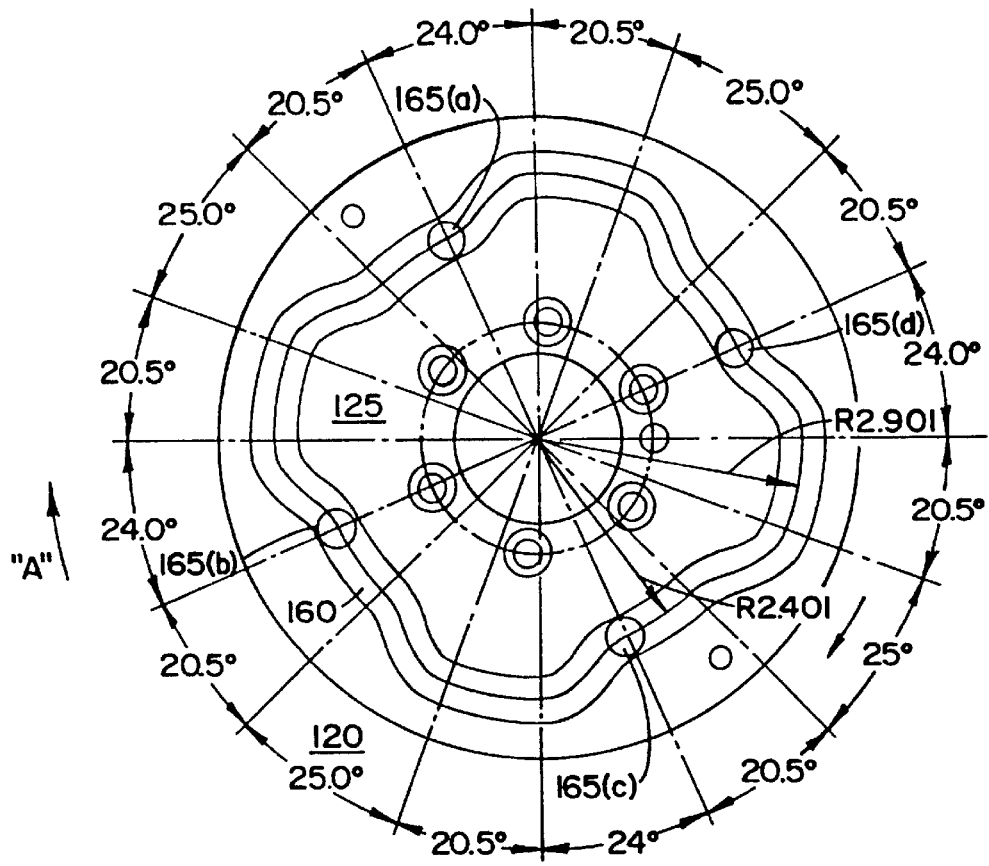

The process for extending each universal gripper 155 for needle processing at each of the stations 100, 200, 400, and 500 will now be explained. As shown in FIGS. 10(a), 10(b) and 10(c), each universal gripper 155 is connected to a reciprocating carriage 151 and a cam slide 164. Cam followers 165(a),(b),(c) and (d) are mounted to a cam slide 164 at one end thereof with the universal gripper at the other end. Cam slide 164 is slidable within stationary guides 166,167 and is adapted for reciprocal movement when the cam follower 165 is actuated. In the preferred embodiment shown in FIG. 11(a), cam follower 165(a) is a roller that fits within cam track of a rotatable cam dial assembly 120. Cam dial assembly 120 is shown in FIG. 11(a) as comprising a cam dial plate 125 having a continuous cam track 160 which receives cam followers 165(a)–(d) attached to universal grippers 155a,b,c, and 155d, respectively. Each cam follower 165 is positioned within the cam track at each station for movement therein.

Figure 11B:
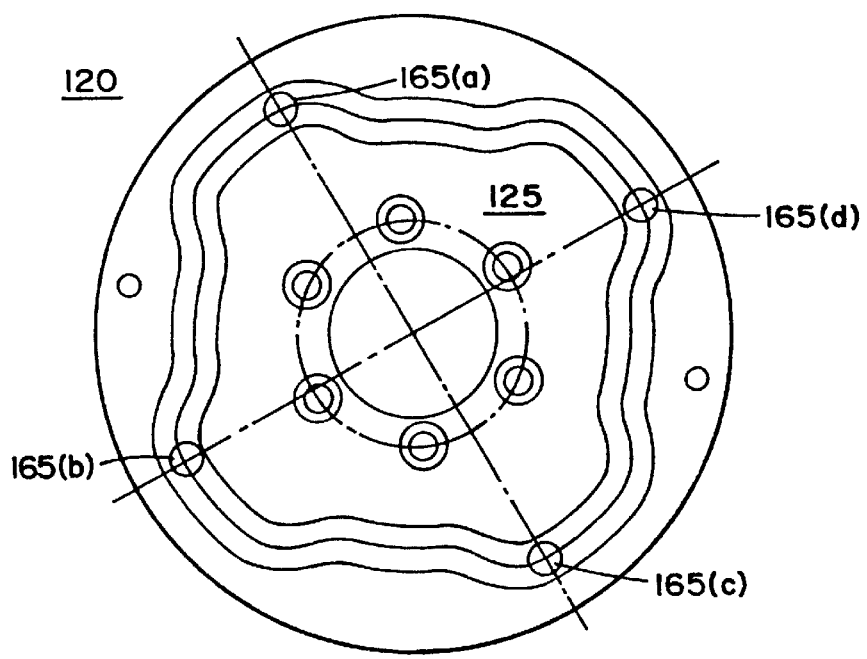

As illustrated in FIG. 11(a), cam dial 125 is positioned above swage dial 110 and mounted coaxial therewith. The cam dial 125 is rotatable about a central axis and controlled by a separate rotary indexing transmission as described previously so that it may rotate separately from the swage dial plate 110. FIG. 11(a) shows cam followers 165(a)–(d) in a first retracted position within the cam track 160. When the dials are in this position, each of the reciprocating carriages and consequently universal grippers 155 are in their retracted position as shown in FIG. 10(a) and 10(b) discussed above. To extend the universal grippers 155 in place at their respective stations, the cam dial plate 125 is rotated in the clockwise direction with respect to the swage dial plate 110, as indicated by the arrow A in FIG. 11(a), for approximately 25 to 45 degrees, forcing cam follower 165a in its cam track 160a to move toward the periphery of the dial as shown in FIG. 11(b). Consequently, each of the cam slides 164, reciprocating carriages 151a, and the universal grippers 155 move to the extended position as shown in FIG. 10(c). To move back to its retracted position, the cam dial plate 125 is rotated in the counter clockwise direction with respect to the swage dial plate 110 for approximately 25–45 degrees, forcing cam follower 165a in its respective cam track 160a to move to its retracted position (FIG. 11(a)). Consequently, the cam slide 164, reciprocating carriage 151a, and the universal gripper 155 move back to the retracted position as shown in FIG. 10(b) and discussed above.

It should be understood that when cam dial plate 125 rotates with respect to swage dial 110, each universal gripper 155 is either extended or retracted by its respective cam track. Thus, the system is designed so that all processes performed at each station occur simultaneously and for approximately the same duration of time when the universal grippers are in their extended position, for e.g., for needle pick-up, for needle swaging, or, for needle pull-testing.

When the universal gripper 155 is retracted, the needle engaged thereby may then be indexed to a different station for further processing. To index the needle to another station, both swage dial plate 110 and cam dial plate 125 are rotated together for approximately 90 degrees to position the universal gripper at the next station. For example, when the cam dial plate 125 and the swage dial plate 110 are simultaneously rotated 90 degrees counterclockwise in FIG. 10, the gripper 155 that had received the needle at station is now indexed to station 200 for swaging a suture thereto. Similarly, after swaging, the cam dial plate 125 and the swage dial plate 110 are simultaneously rotated counterclockwise so that the armed needle at station 200 is indexed to the pull-testing station 400 for pull-testing thereof. The operations performed concurrently at each station about the swage dial increases throughput to provide an output of pull-tested armed surgical needles at a rate of approximately 40 to 60 per minute in the preferred embodiment.

Universal Gripper

As illustrated in FIG. 1, the rotatable swage dial assembly 150 cooperates with four stations where simultaneous needle operations are performed. In the detailed illustration of FIG. 10(a), the swage dial assembly 150 includes a swage plate 110 having four universal gripper stations 145a, 145b, 145c, 145d spaced equally thereon.

The swage plate 110 is rotatably mounted at a central hub 112 on a ball detent safety clutch 114 (illustrated in FIG. 8) and operable to rotate under the control of a control system computer 46. In the preferred embodiment, a separate reciprocating carriage 151 is provided at each universal gripper station of the swage dial assembly 150. For instance, as shown in FIG. 10(a), universal gripper station 145a includes reciprocating carriage 151a, while station 145b includes reciprocating carriage 151b, station 145c includes reciprocating carriage 151c, and station 145d includes reciprocating carriage 151d. Mounted to each reciprocating carriage 151a, b,c,d for retractable movement therewith, is one universal gripper 155, two of which are shown connected to gripper mounts 150(a) and (d) in FIG. 10(a).

As previously mentioned, each reciprocating carriage 151a,b,c,d and universal gripper 155 connected thereto is movable from a retracted position to an extended position. When the gripper 155 is in the retracted position shown in FIG. 10(b), the needle 39 may be conveyed to a different station as the swage dial rotates; when the gripper 155 is in the extended position as shown in FIG. 10(c), the needle is in one of the active stations, such as the automatic swaging station. The swaging station and the automatic pull-test station are both described in further detail in respective copending patent applications Ser. Nos. 08/845,638 and 08/847,132 assigned to the same assignee of the present invention.

The universal gripper of the present invention receives the needle from the precision conveyor and moveable hard stop mechanism, and transports the needle through the swage operation in which a suture is automatically inserted into the barrel end of the needle, and the metal of the needle swaged about the suture. As can be appreciated, when the opening in the barrel is only 0.0106 and the suture diameter is 0.0088, a high degree of precision handling is required, particularly so when the insertion and swage operation need to be completed in approximately 0.5 seconds in order to maintain a 30 to 60 needle per minute cycle rate. The universal gripper also transports the needle through the pull test station in which the suture bond is tested and to the packaging area, where the armed suture (needle and suture assembly) is bundled with other armed sutures for future packaging.

In FIGS. 14(a)(b) and (c), both the slide portion 164 and the gripper portion of the universal gripper 155 are illustrated, with a pair of needle gripping jaws 146 and 148, each having a portion of a needle receiving indent 157 formed therein. Each of the jaws have a reciprocal slide portion 146(a), 148(a) formed as an integral part, which slides reciprocate in a channel 162 formed in housing member 174. The jaws 146 and 148 are biased to each other and to a closed position by a spring member 160. The jaws are opened by a pair of moveable pivot linkages 166, 168 which are mounted to and actuated by plunger 170, so that when plunger 170 is depressed, the linkages 166, 168 are moved outwardly, drawing the jaws 146 and 148 with them. The plunger 170 is actuated by a cam driven by an air motor at each automatic station to open and close the jaws about a needle 39. A cavity 188 is formed in the face of the universal gripper for receiving a needle stripping pin between a needle in jaws 146,148 and the face of the universal gripper.

In the apparatus, a plurality of universal grippers are employed, preferably 4, each of which grips a single needle at positioning, at swaging, at testing and at off-load, as previously described. As the universal gripper is moved into position, the jaws 146,147 are opened and the gripper is reciprocated towards the needle so that open jaws are presented on each side of the needle. The jaws of the precision conveyor boat 70 are then opened, and during transfer, the needle rests on the moveable hard stop 96. The jaws 146,148 of the universal gripper are then closed to grip the needle and the moveable hard stop 96 is reciprocated out of engagement with the needle, and away from the jaws of the precision conveyor to allow the precision conveyor to advance the next needle into the needle transfer position.

The step of loading of the individual precisely oriented surgical needle 39 from the precision conveyor boat 70 and the moveable hard stop 96 onto the universal gripper 155 at the precision loading station 100 involves a compound movement on the part of the universal gripper. Since the needle is gripped in detents formed in the jaws of the conveyor boat 70, and since one of the jaws of the precision conveyor boat 70 is fixed, it is necessary for the universal gripper to transcend a compound movement when removing the needle from the conveyor boat jaws. If a straight reciprocal movement is attempted, the needle is stripped from the jaws of the universal conveyor by the detent in the fixed jaw of the conveyor boat 70. This compound movement is found at both the precision position station 100 and the swage station 200, which also uses fixed and moveable jaws. The use of a fixed jaw substantially improves the accuracy of the alignment of the needle with the suture at the swage station.

In the frontal view of the universal gripper as shown in FIG. 15, jaws 146 and 148 of the universal gripper 155 extend perpendicularly from the gripper to engage the barrel end 44 of the arcuate needle 39.

FIG. 15 also illustrates two roller cam surfaces 172, 180 which act on the universal gripper. A cam surface 172 is found at each of the four stations, (Precise positioning, swage, test and off-load) and is used to open jaws 146 and 148 of the universal gripper at each station. FIGS. 7 and 8 also illustrate three pneumatic drives 176(a),(b) and(c) which actuate rollers 172(a),(b) and (c) to open and close the jaws of the universal gripper 155 as will be hereinafter explained in greater detail.

FIG. 8 illustrates a typical positioning for cam 172 above the needle pull test station, wherein cam roller 172(a) is mounted on a bell crank 174, which is actuated by an air cylinder 176(a). The cam 172(a) is normally biased to a non-engaged position by spring 178.

Each of the universal grippers 155 is mounted for linear movement with respect to the cam slide 164 by means of an off-set slide assembly, the details of which will be explained as with respect to FIGS. 14(a), (b) and (c). As indicated therein, the housing 174 of the universal gripper is mounted on a mounting block 175 and slide 177, and slide 177 is spring biased to a home position during reciprocation within slide carriage 151 by spring member 179. This second reciprocal movement is transverse to the reciprocal movement imparted by cam slide 164.

Referring to FIG. 15, roller cam 180 is used to provide the compound off-set movement of the universal gripper as it is reciprocated outwardly by the swage dial cam plate 125. FIG. 10(a) illustrates a typical positioning for the off-set drive used to drive cam roller 180 at the precise positioning station 100. Roller cam 180 is mounted on a linear slide 182, which is driven by an air motor 184, mounted on the swage dial frame. FIG. 10(a) also illustrates the relative motions of the universal gripper 155, with arrow A indicating the off-set movement, arrow B indicating the reciprocal movement which results in the radial reciprocation of the universal gripper 155 to 155a in FIG. 10(a), and arrow C indicating the rotary motion of the swage dial 110.

To accomplish the transfer of the needle to a universal gripper 155, the universal gripper 155 is extended and translated horizontally so that the face of the universal gripper is adjacent to the needle precision conveyor boat 70 as shown in FIG. 8 and 10(*a*). In this position, the jaws 146 and 148 penetrate the plane of the needle 39 on either side thereof. A load solenoid or similar device depresses a pusher arm of the precision conveyor boat 70 to release the needle from the engagement jaws 77,79 of the precision conveyor boat 70 so that it rests on the movable hard stop assembly between jaws 146 and 148 of the universal gripper 155. Simultaneously therewith, as controlled by the control system computer, jaws 146 and 148 are actuated from the non-engaging position to an engaging position to thereby engage the needle 39 in an oriented position as shown in FIG. 15. The universal gripper 155 is then off-set horizontally and retracted radially and the swage dial assembly 150 is rotated to the swaging station 200 to accomplish automatic swaging of the suture to the needle 39.

Figure 12:
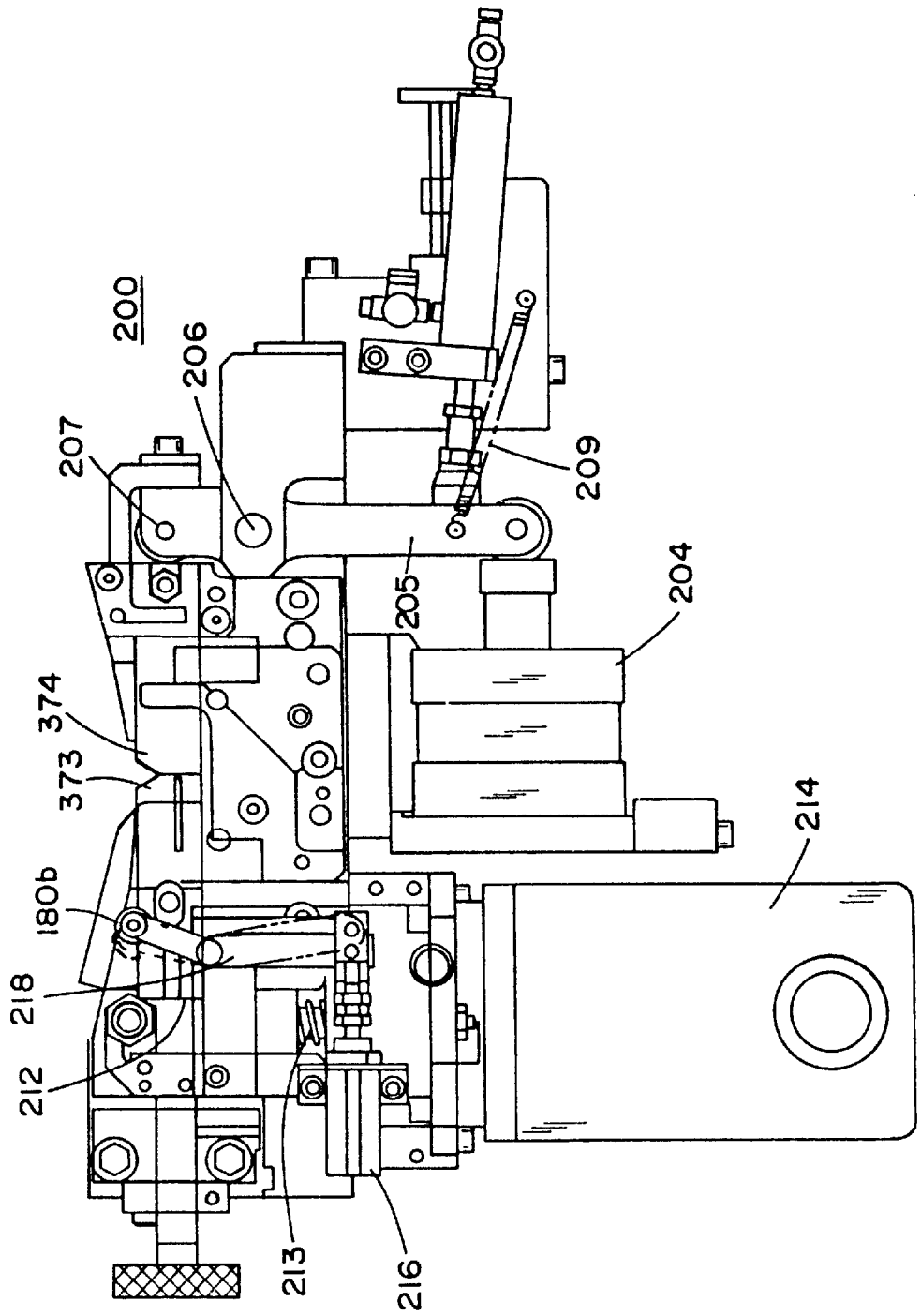
FIG. 12 is a top plan view of the swage assembly and off-set assembly of the present invention used for swaging the needles for suture attachment.

After the tip end 358 of suture 304*a* has been inserted into the barrel end 44 of needle 39, the swage die plates 373,374 are driven together by the swage drive cylinder 204 illustrated in FIG. 12 as more completely described and illustrated in U.S. Ser. No. 08/845,638, entitled "Stand Alone Swage Dial Assembly," also assigned to the assignee of the present invention, the disclosure of which is incorporated herein by reference thereto.

As illustrated in FIG. 12, the moveable swage die 374 is driven by air cylinder 204 through a bell crank 205 which pivots about pivot point 206 by virtue of its attachment at 207. The fixed die plate 373 is relatively fixed, and bears against a sliding angled anvil 212 which may be advanced by motor 214 through drive screw 213. This enables very precise adjustments of the amount of swage pressure applied to the swage dies 373, 374 and the needle 39 during the swage operation. The universal gripper is off-set during entry and egress by cam roller 180(*b*), which is driven by air cylinder 216 through bell crank 218. This off-set is necessary to allow the needle to clear the swage die opening in the fixed swage die as it is placed in position by the universal gripper 155.

Referring to FIG. 15, after the needle has been swaged to the suture, the universal gripper 155 closes jaws 146,148 on needle barrel end 44 as the drive roller 172 is reciprocated out of engagement with plunger 170. Simultaneously therewith, the moveable swage plate 374 is retracted to enable movement of needle 39 by the universal gripper 155. Before the swage dial 110 is rotated, the offset drive cam roller 180(*b*) is again advanced to bear against cam plate 186 and provide egress of the needle 39 from the swage dye cavity in fixed swage plate 373. Once the universal gripper 155 and needle 39 have cleared the fixed swage plate, the cam dial assembly 120 is rotated advancing cam rollers 165 inwardly to retract the universal grippers 155 in a radial direction and enable rotation of the swage dial 110.

Swage dial 110 then rotates the needle and suture assembly to a pull test station for testing as described in U.S. Ser. No. 08/847,132, entitled "Pull Test Station for Permanently Attached Sutures," also assigned to the assignee of the present invention, the disclosure of which is incorporated herein by reference thereto.

Figure 16:
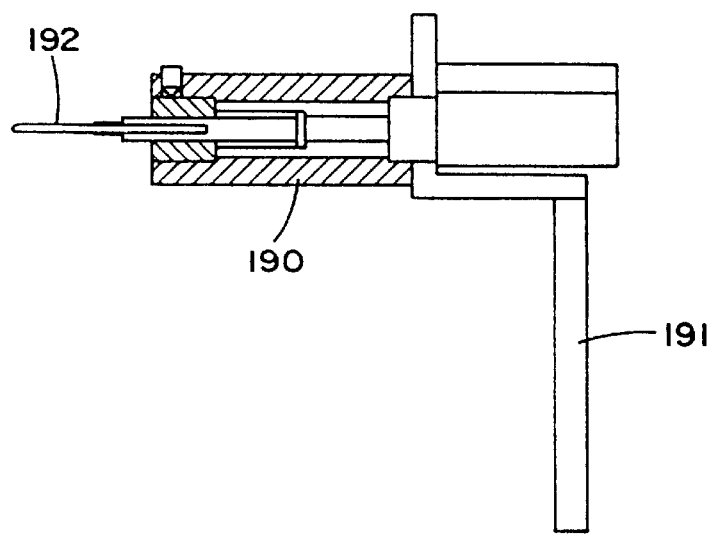
FIG. 16 is a partially cross section top view of the needle stripper assembly used in the present invention.

The present invention includes a pair of needle strippers, one of which is illustrated in FIG. 16. The locations of needle strippers 190*a*,190*b*, are illustrated in FIG. 10(*a*) adjacent the circumference of the swage dial plate 110. Needle stripper assemblies 190(*a*),(*b*) are mounted to the frame of the standalone swage machine by means of brackets 191*a*,191*b* to provide a longitudinal axis of reciprocation for the needle stripping pins 192*a,b* that is tangential to the circumference described by the face of the universal grippers 155. When the needle stripper pins 192 are retracted, as illustrated in FIG. 16, the universal gripper passes the needle stripping station without engagement. However, when the needle stripping pins are reciprocated outwardly, they intercept the path of needle 39 and are positioned to reciprocate into a space 188 defined between the face of the universal gripper 155 and the needle 39. Simultaneously therewith, the plunger 170 on the universal gripper is depressed by one of the offload cams 172 to open the jaws 146,148 of the universal gripper and enable the needle to be stripped from the universal gripper.

The needle stripper assembly 190(*a*) illustrated in FIG. 10(*a*) is used to remove needles that have failed the pull test at the pull test station 400. The needle stripper assembly 190(*b*) is used to remove the needle and suture assembly from the universal gripper for bundling in the offload station 500.

Figure 17B:
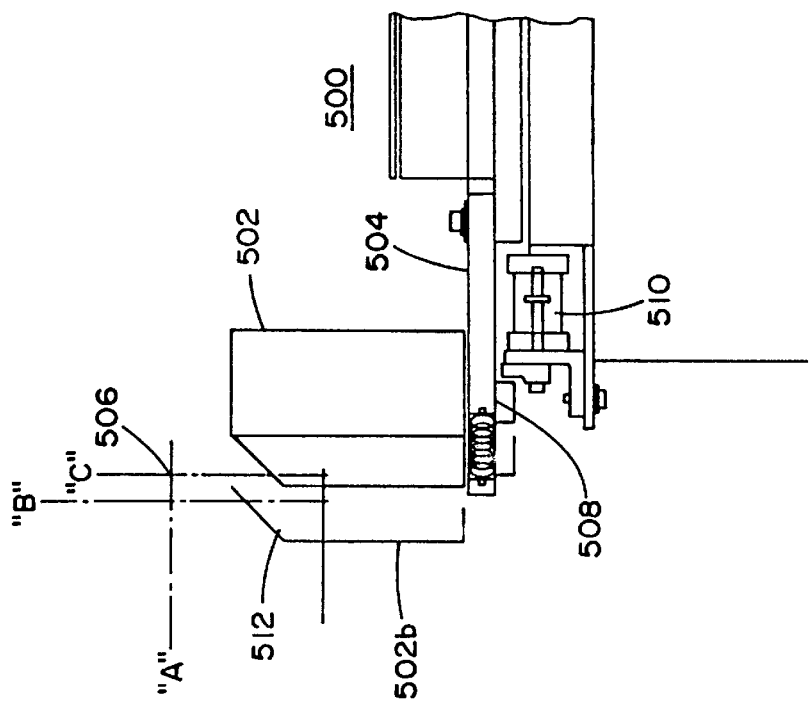
FIG. 17(b) is a partially cross sectioned side view of one of the bundle receiving compartments illustrated in FIG. 17(a).
Figure 17A:
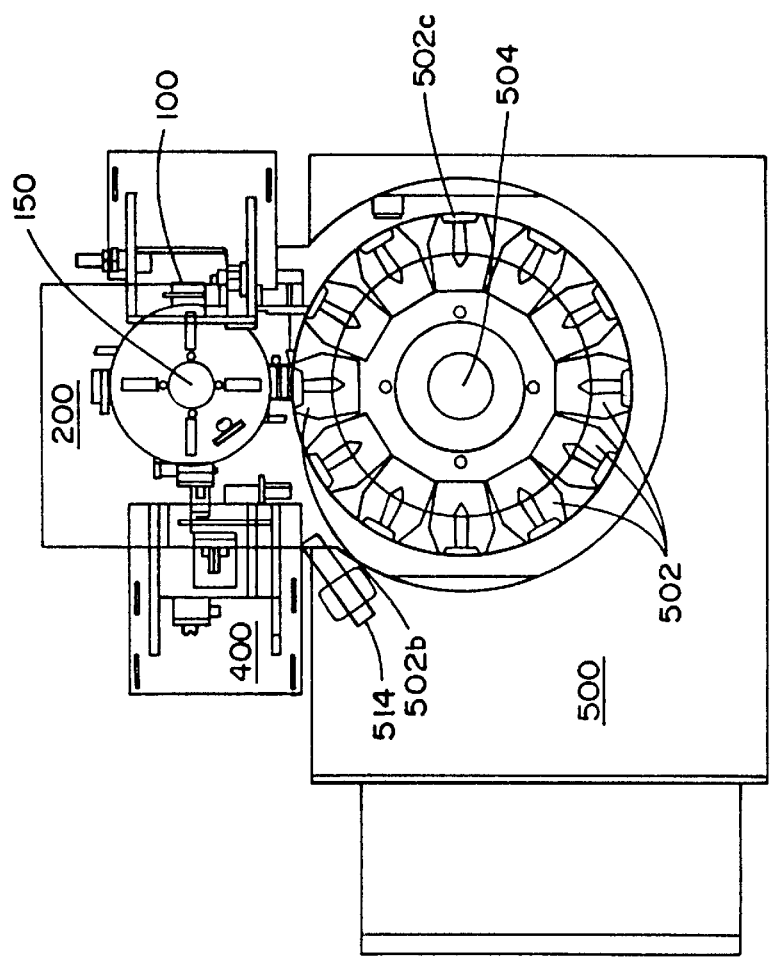
FIG. 17(a) is a top plan view of the needle bundling station of the present invention illustrating a plurality of compartments, each of which receives a predetermined number of needle and suture assemblies.

The offload station 500 is more particularly illustrated and described with respect to FIGS. 17*a* and 17*b* in which a plurality of needle buckets 502 are circumferentially arranged on a rotatable turntable 504 to be indexed under the collection point 506 defined by the intercept axis of the needle stripper pin and the face of the universal gripper 155. As illustrated in FIG. 17*b*, dotted line axis A illustrates the circumferential path of the needle in a horizontal plane while axis B and C illustrate the radial reciprocation of the universal gripper 155. The needle stripping pin 192*b* engages the needle at the intersection of axis A and C at 506 causing the needle to drop into the needle bucket 502. Each of the needle buckets 502 is spring mounted for radial reciprocation on turntable 504 by means of a spring loaded reciprocating mount 508 which nominally biases the needle bucket 502 inwardly. When the needle bucket has arrived at the offload position, the bucket 502 is reciprocated outwardly as illustrated in FIG. 17*b* by a pneumatic motor 510 to the position 502*b* illustrated in FIG. 17*b*.

As the needle is stripped from the universal gripper, it falls to the interior of the bucket, with a suture draped over a bundling edge 512. If desired, a plurality of pins may be arrayed along 512 to prevent entanglement of the sutures. In addition, a stream of deionized air may be provided at this station to assist in the orderly collection of the sutures following the swage assembly.

FIG. 17(*a*) also illustrates a detector 514 which is focused on a reflector plate under the swage dial assembly 150 that is triggered by a passing suture to actuate the needle stripping assembly 190(*b*).

After a predetermined number of needle and suture assemblies have been collected in the needle bucket 502, the needle bucket 502 is reciprocated inwardly by relaxing air motor 510 and the turntable 504 is indexed to position the next available needle bucket 502 under the offload station. While 12 offload buckets 502 have been illustrated in FIG. 17(*a*), it is understood that a smaller number of buckets could be used if desired.

After a needle bucket 502 has been filled with a predetermined number of needle and suture assemblies, and rotated to the position illustrated at 502(*c*) in FIG. 17*a*, the bundle of needle and suture assemblies may be removed for subsequent handling and packaging.

As is readily apparent to one skilled in the art, many variations on the above described embodiment are possible. The foregoing description is exemplary only and not to be construed as limiting the scope of the invention, which is defined in the claims, as follows.

What is claimed:

1. A needle threading and swaging apparatus for attaching a suture to a surgical needle having a suture receiving opening formed therein, said apparatus comprising:

(a) a frame for said apparatus, said frame supporting a drive means, said drive means including a first and a second intermittent drive, each of said intermittent drives having a drive period and a dwell period;

(b) a swage dial and a cam dial mounted for rotation about a first axis of rotation, said swage dial mounted for rotation on a first drive shaft which rotates about said first axis of rotation, said drive shaft driven by said first intermittent drive;

(c) a plurality of universal gripper mounted on said swage dial for successively receiving an individual one of a plurality of precisely positioned needles at a first predetermined location and indexing each of said individual successive needles in a predetermined orientation from said first predetermined location through successive locations for sequential processing at subsequent predetermined locations, each of said universal grippers having a cam follower which cooperates with said cam dial to provide radial reciprocation of said universal grippers with respect to said swage dial in response to rotation of said cam dial;

(d) an annular drive shaft mounted on said first drive shaft, said annular drive shaft coupling said second intermittent drive and said cam dial for rotation about said first axis;

whereby said universal grippers are rotated by said swage dial to each of said predetermined locations and reciprocated by said cam dial at each of said plurality of predetermined locations.

2. The needle threading and swaging apparatus according to claim 1 wherein said swage dial is coupled to said first drive shaft by a breakaway clutch.

3. The needle threading and swaging apparatus according to claim 1 wherein said first and said second intermittent drives are coupled and driven by a single motor.

4. The needle threading and swaging apparatus according to claim 3 wherein each of said intermittent drives include 180 degrees of dwell and 180 degrees of rotation.

5. The needle threading and swaging apparatus according to claim 1 wherein said apparatus further includes at least one off-set drive at least one of said predetermined locations to engage said universal gripper during radial reciprocation thereof to provide a compound movement during radial reciprocation from a first retracted position to a second extended position with respect to said swage dial.

6. The needle threading and swaging apparatus according to claim 1 wherein said apparatus further includes one of said off-set drives at a first predetermined location for precise engagement of said needles and a second one of said off-set drives at a subsequent predetermined swage location.

7. The needle threading and swaging apparatus according to claim 5 wherein said universal gripper means includes first and second jaws for engaging said surgical needle, said jaws having a first engaging position for engaging said surgical needle in a precisely oriented position, and a second non-engaging position for releasing said surgical needle.

8. The needle threading and swaging apparatus according to claim 7 wherein each of said universal grippers is mounted on said swage dial with a spring loaded linear slide, wherein said gripper is reciprocated in a radial direction by said cam plate, and reciprocated transversely thereto along said linear slide by said off-set drive.

9. The needle threading and swaging apparatus according to claim 2 wherein said first shaft is journalled for rotation in said frame, and supports said swage dial through said breakaway clutch.

10. A needle threading and swaging apparatus for attaching a suture to a surgical needle having a suture receiving opening formed therein, said apparatus comprising:

(a) a frame for said apparatus, said frame supporting a drive means, said drive means including a first and a second intermittent drive, each of said intermittent drives having a drive period and a dwell period;

(b) a swage dial and a cam dial mounted for rotation about a first axis of rotation, said swage dial mounted for rotation on a first drive shaft which rotates about said first axis of rotation, said drive shaft driven by said first intermittent drive;

(c) a plurality of universal gripper mounted on said swage dial for successively receiving an individual one of a plurality of precisely positioned needles at a first predetermined location and indexing each of said individual successive needles in a predetermined orientation from said first predetermined location through successive locations for sequential processing at subsequent predetermined locations, each of said universal grippers having a cam follower which cooperates with said cam dial to provide radial reciprocation of said universal grippers with respect to said swage dial in response to rotation of said cam dial;

(d) an annular drive shaft mounted on said first drive shaft, said annular drive shaft coupling said second intermittent drive and said cam dial for rotation about said first axis;

(e) a suture insertion station located at a second predetermined location for automatically inserting a suture of predetermined length into said suture receiving opening formed in said surgical needle;

(e) a needle swaging station for swaging said surgical needle to close said suture receiving opening about a free end of said suture to secure said suture thereto and form therefrom a needle and suture assembly, (f) means for receiving individual needle and suture assemblies from said universal gripper and accumulating a predetermined number thereof to provide a bundle of needle suture assemblies for subsequent packaging;

whereby unsorted needles and lengths of suture material are formed into a bundle of surgical needle and suture assemblies.

11. The needle threading and swaging apparatus according to claim 10 wherein said universal gripper means includes a compound movement during radial reciprocation from a first retracted position to a second extended position with respect to said swage dial.

12. The needle threading and swaging apparatus according to claim 11 wherein said universal gripper means includes first and second jaws for engaging said surgical needle, said jaws having a first engaging position for engaging said surgical needle in a precisely oriented position, and a second non-engaging position for releasing said surgical needle.

13. The needle threading and swaging apparatus according to claim 12, wherein said suture insertion station further includes means for cutting said suture of predetermined length from an indefinite length suture, said station further comprising:

(a) a drawing frame, said frame having at least one longitudinal member and defining a drawing axis parallel thereto;

(b) means for feeding a flexible indefinite length suture strand to said drawing axis for drawing and cutting;

(c) first and second gripping means for gripping said indefinite length suture strand and drawing it along said drawing axis, said first gripping means mounted for reciprocal movement on said at least one longitudinal member;

(d) means for cutting said indefinite length suture strand to form said suture of predetermined length; and (e) said second gripping means reciprocal to a start position along said drawing axis and below said cutting means, while said first drawing means is drawing said indefinite length suture strand to an insertion zone located a predetermined distance beyond said cutting means, whereby said suture of predetermined length is inserted within said suture receiving opening of said needle and cut to a predetermined length by said cutting means after said second gripping means has gripped said indefinite length suture strand at said start position.

14. The needle threading and swaging apparatus according to claim 13 wherein said needle swaging station includes first and second swaging die means, said first swaging die means having an end thereof defining a portion of a swage die opening, and said second swaging die means having an end thereof defining another portion of said swage die opening, wherein said second swaging die means is positioned next to said first swaging die means to form a swage die opening for receiving said needle.

15. The needle threading and swaging apparatus according to claim 14, wherein said first swaging die means is fixed in position and said second swaging die means is laterally movable toward and away from said first fixed swage die means.

16. The needle threading and swaging apparatus according to claim 15, wherein said swage die opening is axially aligned with said drawing axis at said swaging station, with said universal gripper means in said retracted position prior to positioning said surgical needle within said swage die opening, and is extended and translated in a compound movement to position said suture receiving opening of said needle in said swage die opening prior to swaging.

17. The needle threading and swaging apparatus according to claim 16 wherein said swaging station further includes a funnel guide means positioned at said insertion zone between a free end of said definite length suture strand and said suture receiving opening of said needle, said funnel die means including a tapered opening axially aligned with said swage die opening for directing said free end of said suture strand into said suture receiving opening of said needle positioned therein.

18. The needle threading and swaging apparatus according to claim 10 wherein said swage dial is coupled to said first drive shaft by a breakaway clutch.

19. The needle threading and swaging apparatus according to claim 10 wherein said first and said second intermittent drives are coupled and driven by a single motor.

20. The needle threading and swaging apparatus according to claim 19 wherein each of said intermittent drives include 180 degrees of dwell and 180 degrees of rotation for each two revolutions of said motor, wherein said swage dial is advanced in 90 degree increments and said cam dial is rotated in 90 degree increments that are out of phase with respect to said swage dial.

21. The needle threading and swaging apparatus according to claim 14 wherein said apparatus further includes at least one off-set drive at least one of said predetermined locations to engage said universal gripper during radial reciprocation thereof to provide a compound movement during radial reciprocation from a first retracted position to a second extended position with respect to said swage dial.

22. The needle threading and swaging apparatus according to claim 21 wherein said apparatus further includes one of said off-set drives at a first predetermined location for precise engagement of said needles and a second one of said off-set drives at said swaging station.

23. The needle threading and swaging apparatus according to claim 21 wherein said universal gripper means includes first and second jaws for engaging said surgical needle, said jaws having a first engaging position for engaging said surgical needle in a precisely oriented position, and a second non-engaging position for releasing said surgical needle.

24. The needle threading and swaging apparatus according to claim 23 wherein each of said universal grippers is mounted on said swage dial with a spring loaded linear slide, wherein said gripper is reciprocated in a radial direction by said cam plate, and reciprocated transversely thereto along said linear slide by said off-set drive.

25. The needle threading and swaging apparatus according to claim 10 wherein said first shaft is journalled for rotation in said frame, and supports said swage dial during rotation thereof through said breakaway clutch.

* * * * *